(12) United States Patent
Pamula et al.

(10) Patent No.: US 10,585,090 B2
(45) Date of Patent: Mar. 10, 2020

(54) BEAD INCUBATION AND WASHING ON A DROPLET ACTUATOR

(71) Applicant: Advanced Liquid Logic, Inc., San Diego, CA (US)

(72) Inventors: Vamsee K. Pamula, Cary, NC (US); Michael G. Pollack, Durham, NC (US); Ramakrishna Sista, Cary, NC (US); Arjun Sudarsan, Carlsbad, CA (US)

(73) Assignee: ADVANCED LIQUID LOGIC, INC., San Diego, CA (US)

( * ) Notice: Subject to any disclaimer, the term of this patent is extended or adjusted under 35 U.S.C. 154(b) by 0 days.

(21) Appl. No.: 16/132,175

(22) Filed: Sep. 14, 2018

(65) Prior Publication Data

US 2019/0011443 A1    Jan. 10, 2019

Related U.S. Application Data

(60) Division of application No. 15/210,634, filed on Jul. 14, 2016, now Pat. No. 10,078,078, which is a
(Continued)

(51) Int. Cl.
*G01N 15/06* (2006.01)
*G01N 33/00* (2006.01)
(Continued)

(52) U.S. Cl.
CPC .... *G01N 33/54333* (2013.01); *B01F 11/0071* (2013.01); *B01F 13/0071* (2013.01);
(Continued)

(58) Field of Classification Search
CPC ........ G01N 15/06; G01N 33/00; G01N 33/48; G01N 33/54333; G01N 35/00; G01N 1/00;
(Continued)

(56) References Cited

U.S. PATENT DOCUMENTS

| 4,127,460 | A | 11/1978 | Gaske |
| 4,244,693 | A | 1/1981 | Guon |

(Continued)

FOREIGN PATENT DOCUMENTS

| JP | 2006-500596 | 1/2006 |
| JP | 2006-078225 | 3/2006 |

(Continued)

OTHER PUBLICATIONS

Published Abstract from NIH Grant Project No. CA114993.
(Continued)

*Primary Examiner* — Brian J. Sines
(74) *Attorney, Agent, or Firm* — Illumina, Inc.

(57) ABSTRACT

Methods are provided for separating magnetically responsive beads from a droplet in a droplet actuator. Droplet operations electrodes and a magnet are arranged in a droplet actuator to manipulate a bead-containing droplet and position it relative to a magnetic field region that attracts the magnetically responsive beads. The droplet operations electrodes are operated to control the droplet shape and transport it away from the magnetic field region to form a concentration of beads in the droplet. The continued transport of the droplet away from the magnetic field causes the concentration of beads to break away from the droplet to yield a small, concentrated bead-containing droplet immobilized by the magnet.

20 Claims, 19 Drawing Sheets

Related U.S. Application Data continuation of application No. 14/731,740, filed on Jun. 5, 2015, now Pat. No. 9,395,361, which is a continuation of application No. 14/466,193, filed on Aug. 22, 2014, now Pat. No. 9,081,007, which is a continuation of application No. 14/081,376, filed on Nov. 15, 2013, now Pat. No. 8,846,410, which is a division of application No. 13/081,927, filed on Apr. 7, 2011, now Pat. No. 8,637,324, said application No. 14/466,193 is a continuation-in-part of application No. 12/615,666, filed on Nov. 10, 2009, now Pat. No. 8,951,721, and a continuation-in-part of application No. 12/615,609, filed on Nov. 10, 2009, now Pat. No. 8,313,895, said application No. 13/081,927 is a continuation of application No. PCT/US2009/059868, filed on Oct. 7, 2009, said application No. 12/615,609 is a continuation-in-part of application No. 12/113,385, filed on May 1, 2008, now Pat. No. 8,541,176, said application No. 12/615,666 is a continuation of application No. 12/113,385, filed on May 1, 2008, now Pat. No. 8,541,176, said application No. 14/466,193 is a continuation of application No. 12/113,385, filed on May 1, 2008, now Pat. No. 8,541,176, said application No. 13/081,927 is a continuation-in-part of application No. 11/639,531, filed on Dec. 15, 2006, now Pat. No. 8,613,889, said application No. 12/113,385 is a division of application No. 11/639,736, filed on Dec. 15, 2006, now Pat. No. 7,439,014, said application No. 14/466,193 is a continuation-in-part of application No. 11/639,736, filed on Dec. 15, 2006, now Pat. No. 7,439,014.

(60) Provisional application No. 61/122,791, filed on Dec. 16, 2008, provisional application No. 61/103,302, filed on Oct. 7, 2008, provisional application No. 60/807,104, filed on Jul. 12, 2006, provisional application No. 60/806,412, filed on Jun. 30, 2006, provisional application No. 60/746,801, filed on May 9, 2006, provisional application No. 60/746,797, filed on May 9, 2006, provisional application No. 60/745,914, filed on Apr. 28, 2006, provisional application No. 60/745,950, filed on Apr. 28, 2006, provisional application No. 60/745,039, filed on Apr. 18, 2006, provisional application No. 60/745,058, filed on Apr. 18, 2006, provisional application No. 60/745,059, filed on Apr. 18, 2006, provisional application No. 60/745,043, filed on Apr. 18, 2006.

(51) Int. Cl.

| | | |
|---|---|---|
| *G01N 33/48* | (2006.01) | |
| *G01N 35/00* | (2006.01) | |
| *G01N 1/00* | (2006.01) | |
| *G01N 1/10* | (2006.01) | |
| *B01L 3/00* | (2006.01) | |
| *G01N 33/543* | (2006.01) | |
| *B01F 13/00* | (2006.01) | |
| *B03C 1/02* | (2006.01) | |
| *B03C 1/28* | (2006.01) | |
| *B03C 1/30* | (2006.01) | |
| *B03C 5/00* | (2006.01) | |
| *C12N 15/10* | (2006.01) | |
| *G01N 33/561* | (2006.01) | |
| *B01F 11/00* | (2006.01) | |
| *B01L 7/00* | (2006.01) | |
| *G01N 35/10* | (2006.01) | |

(52) U.S. Cl.
CPC .... *B01F 13/0076* (2013.01); *B01L 3/502715* (2013.01); *B01L 3/502761* (2013.01); *B01L 3/502784* (2013.01); *B01L 3/502792* (2013.01); *B03C 1/02* (2013.01); *B03C 1/288* (2013.01); *B03C 1/30* (2013.01); *B03C 5/005* (2013.01); *C12N 15/1013* (2013.01); *G01N 33/561* (2013.01); *B01L 7/52* (2013.01); *B01L 7/525* (2013.01); *B01L 2200/027* (2013.01); *B01L 2200/0647* (2013.01); *B01L 2200/0668* (2013.01); *B01L 2300/0654* (2013.01); *B01L 2300/089* (2013.01); *B01L 2300/0816* (2013.01); *B01L 2300/0861* (2013.01); *B01L 2300/0864* (2013.01); *B01L 2300/0867* (2013.01); *B01L 2300/1827* (2013.01); *B01L 2400/043* (2013.01); *B01L 2400/0406* (2013.01); *B01L 2400/0415* (2013.01); *B01L 2400/0421* (2013.01); *B01L 2400/0424* (2013.01); *B01L 2400/0427* (2013.01); *B01L 2400/0436* (2013.01); *B01L 2400/0442* (2013.01); *B03C 2201/18* (2013.01); *B03C 2201/26* (2013.01); *G01N 2035/1046* (2013.01); *Y10T 436/11* (2015.01); *Y10T 436/25* (2015.01); *Y10T 436/2575* (2015.01); *Y10T 436/25625* (2015.01)

(58) Field of Classification Search
CPC ... G01N 1/10; B01F 11/0071; B01F 13/0071; B01F 13/0076; B01L 3/00; B01L 3/502715; B01L 3/502761; B01L 3/502784; B01L 3/502792; B03C 1/02; B03C 1/288; B03C 1/30
See application file for complete search history.

(56) References Cited

U.S. PATENT DOCUMENTS

| | | |
|---|---|---|
| 4,390,403 A | 6/1983 | Batchelder |
| 4,454,232 A | 6/1984 | Breglio et al. |
| 4,636,785 A | 1/1987 | Le Pesant |
| 4,863,849 A | 9/1989 | Melamede |
| 5,038,852 A | 8/1991 | Johnson et al. |
| 5,176,203 A | 1/1993 | Larzul |
| 5,181,016 A | 1/1993 | Lee et al. |
| 5,225,332 A | 7/1993 | Weaver et al. |
| 5,240,994 A | 8/1993 | Brink et al. |
| 5,266,498 A | 11/1993 | Tarcha et al. |
| 5,455,008 A | 10/1995 | Earley et al. |
| 5,472,881 A | 12/1995 | Beebe |
| 5,486,337 A | 1/1996 | Ohkawa et al. |
| 5,498,392 A | 3/1996 | Wilding et al. |
| 5,720,923 A | 2/1998 | Haff et al. |
| 5,721,851 A | 2/1998 | Cline et al. |
| 5,770,391 A | 6/1998 | Foote |
| 5,770,457 A | 6/1998 | Stocker |
| 5,779,977 A | 7/1998 | Haff et al. |
| 5,817,526 A | 10/1998 | Kinoshita et al. |
| 5,827,480 A | 10/1998 | Haff et al. |
| 5,846,396 A | 12/1998 | Zanzucchi et al. |
| 5,851,769 A | 12/1998 | Gray |
| 5,945,281 A | 8/1999 | Prabhu et al. |
| 5,980,719 A | 11/1999 | Cherukuri et al. |
| 5,998,224 A | 12/1999 | Rohr et al. |
| 6,013,531 A | 1/2000 | Wang et al. |
| 6,033,880 A | 3/2000 | Haff et al. |
| 6,063,339 A | 5/2000 | Tisone et al. |
| 6,106,685 A | 8/2000 | McBride |
| 6,130,098 A | 10/2000 | Handique et al. |
| 6,152,181 A | 11/2000 | Wapner et al. |
| 6,180,372 B1 | 1/2001 | Franzen |
| 6,210,891 B1 | 4/2001 | Nyren et al. |
| 6,258,568 B1 | 7/2001 | Nyren |

(56) References Cited

U.S. PATENT DOCUMENTS

| | | |
|---|---|---|
| 6,294,063 B1 | 9/2001 | Becker et al. |
| 6,319,668 B1 | 11/2001 | Nova et al. |
| 6,379,929 B1 | 4/2002 | Burns et al. |
| 6,432,290 B1 | 8/2002 | Harrison et al. |
| 6,453,928 B1 | 9/2002 | Kaplan et al. |
| 6,454,924 B2 | 9/2002 | Jedrzejewski et al. |
| 6,461,570 B2 | 10/2002 | Ishihara et al. |
| 6,473,492 B2 | 10/2002 | Prins |
| 6,485,913 B1 | 11/2002 | Becker |
| 6,538,823 B2 | 3/2003 | Kroupenkine et al. |
| 6,545,815 B2 | 4/2003 | Kroupenkine et al. |
| 6,548,311 B1 | 4/2003 | Knoll |
| 6,565,727 B1 | 5/2003 | Shenderov et al. |
| 6,596,238 B1 | 6/2003 | Belder |
| 6,591,852 B1 | 7/2003 | McNeely et al. |
| 6,613,560 B1 | 9/2003 | Tso |
| 6,629,826 B2 | 10/2003 | Yoon |
| 6,632,655 B1 | 10/2003 | Mehta et al. |
| 6,665,127 B2 | 12/2003 | Bao et al. |
| 6,673,533 B1 | 1/2004 | Wohlstadter et al. |
| 6,734,436 B2 | 5/2004 | Faris et al. |
| 6,761,962 B2 | 7/2004 | Bentsen |
| 6,773,566 B2 | 8/2004 | Shenderov et al. |
| 6,790,011 B1 | 9/2004 | Le Pesant et al. |
| 6,828,100 B1 | 12/2004 | Ronaghi |
| 6,841,128 B2 | 1/2005 | Kambara |
| 6,846,638 B2 | 1/2005 | Shipwash |
| 6,849,461 B2 | 2/2005 | Eigen et al. |
| 6,868,875 B2 | 3/2005 | De Beukeleer |
| 6,896,855 B1 | 5/2005 | Kohler et al. |
| 6,911,132 B2 | 6/2005 | Pamula et al. |
| 6,924,792 B1 | 8/2005 | Jessop |
| 6,942,776 B2 | 9/2005 | Medoro |
| 6,949,176 B2 | 9/2005 | Vacca et al. |
| 6,955,881 B2 | 10/2005 | Tanaami |
| 6,958,132 B2 | 10/2005 | Chiou et al. |
| 6,960,437 B2 | 11/2005 | Enzelberger et al. |
| 6,977,033 B2 | 12/2005 | Becker et al. |
| 6,989,234 B2 | 1/2006 | Kolar et al. |
| 6,995,024 B2 | 2/2006 | Smith et al. |
| 7,052,244 B2 | 5/2006 | Fouillet et al. |
| 7,078,168 B2 | 7/2006 | Sylvan et al. |
| 7,163,612 B2 | 1/2007 | Sterling et al. |
| 7,189,359 B2 | 3/2007 | Yuan |
| 7,189,560 B2 | 3/2007 | Kim et al. |
| 7,211,223 B2 | 5/2007 | Fouillet et al. |
| 7,211,442 B2 | 5/2007 | Gilbert et al. |
| 7,251,392 B2 | 7/2007 | Kuiper et al. |
| 7,255,780 B2 | 8/2007 | Shenderov |
| 7,267,752 B2 | 9/2007 | King et al. |
| 7,294,503 B2 | 11/2007 | Quake et al. |
| 7,310,080 B2 | 12/2007 | Jessop |
| 7,314,567 B2 | 1/2008 | Wagler et al. |
| 7,328,979 B2 | 2/2008 | Decre et al. |
| 7,329,545 B2 | 2/2008 | Pamula et al. |
| 7,438,860 B2 | 10/2008 | Takagi et al. |
| 7,439,014 B2 | 10/2008 | Pamula et al. |
| 7,454,988 B2 | 11/2008 | Tan |
| 7,458,661 B2 | 12/2008 | Kim et al. |
| 7,459,311 B2 | 12/2008 | Nyren et al. |
| 7,495,031 B2 | 2/2009 | Sakuma et al. |
| 7,531,072 B2 | 5/2009 | Roux et al. |
| 7,547,380 B2 | 6/2009 | Velev |
| 7,556,776 B2 | 7/2009 | Fraden et al. |
| 7,569,129 B2 | 8/2009 | Pamula et al. |
| 7,579,172 B2 | 8/2009 | Cho et al. |
| 7,488,451 B2 | 9/2009 | Sarowitz et al. |
| 7,641,779 B2 | 1/2010 | Becker et al. |
| 7,693,666 B2 | 6/2010 | Griffith et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,767,147 B2 | 8/2010 | Adachi et al. |
| 7,767,435 B2 | 8/2010 | Chiu et al. |
| 7,815,871 B2 | 10/2010 | Pamula et al. |
| 7,816,121 B2 | 10/2010 | Pollack et al. |
| 7,821,699 B1 | 10/2010 | Lo et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger |
| 8,093,064 B2 | 1/2012 | Shah et al. |
| 8,137,917 B2 | 3/2012 | Pollack et al. |
| 8,147,668 B2 | 4/2012 | Pollack et al. |
| 8,179,216 B2 | 5/2012 | Knospe |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,292,798 B2 | 10/2012 | Califorrniaa |
| 8,304,253 B2 | 11/2012 | Yi et al. |
| 8,313,698 B2 | 11/2012 | Pollack et al. |
| 8,317,990 B2 | 11/2012 | Pamula et al. |
| 8,337,778 B2 | 12/2012 | Stone et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 8,470,606 B2 | 6/2013 | Srinivasan et al. |
| 8,492,168 B2 | 7/2013 | Srinivasan |
| 8,658,111 B2 | 2/2014 | Srinivasan et al. |
| 8,980,198 B2 | 3/2015 | Srinivasan et al. |
| 2002/0001544 A1 | 1/2002 | Hess et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0055167 A1 | 5/2002 | Pourahmadi et al. |
| 2002/0058332 A1 | 5/2002 | Quake et al. |
| 2002/0093651 A1 | 7/2002 | Roe et al. |
| 2002/0102595 A1 | 8/2002 | Davis |
| 2002/0128546 A1 | 9/2002 | Silver |
| 2002/0125135 A1 | 10/2002 | Derand et al. |
| 2002/0142483 A1 | 10/2002 | Yao et al. |
| 2002/0143437 A1 | 10/2002 | Handique et al. |
| 2002/0168671 A1 | 11/2002 | Burns et al. |
| 2002/0172969 A1 | 11/2002 | Burns et al. |
| 2002/0176804 A1 | 11/2002 | Strand et al. |
| 2003/0006140 A1 | 1/2003 | Vacca et al. |
| 2003/0007898 A1 | 1/2003 | Bohm et al. |
| 2003/0012483 A1 | 1/2003 | Ticknor et al. |
| 2003/0012699 A1 | 1/2003 | Moore et al. |
| 2003/0015425 A1 | 1/2003 | Bohm et al. |
| 2003/0049177 A1 | 3/2003 | Smith et al. |
| 2003/0082081 A1 | 5/2003 | Fouillet et al. |
| 2003/0103021 A1 | 6/2003 | Young et al. |
| 2003/0108452 A1 | 6/2003 | Fuhr et al. |
| 2003/0119057 A1 | 6/2003 | Gascoyne et al. |
| 2003/0129646 A1 | 7/2003 | Briscoe et al. |
| 2003/0155034 A1 | 8/2003 | De Beukeleer et al. |
| 2003/0164295 A1 | 9/2003 | Sterling |
| 2003/0170613 A1 | 9/2003 | Straus |
| 2003/0170686 A1 | 9/2003 | Hoet et al. |
| 2003/0183525 A1 | 10/2003 | Elrod et al. |

(56) References Cited

U.S. PATENT DOCUMENTS

| | | |
|---|---|---|
| 2003/0198576 A1 | 10/2003 | Coyne et al. |
| 2003/0205632 A1 | 11/2003 | Kim et al. |
| 2003/0206351 A1 | 11/2003 | Kroupenkine |
| 2003/0211009 A1 | 11/2003 | Buchanan |
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0031688 A1 | 2/2004 | Shenderov |
| 2004/0042721 A1 | 3/2004 | Kroupenkine et al. |
| 2004/0055536 A1 | 3/2004 | Kolar et al. |
| 2004/0055871 A1 | 3/2004 | Walton et al. |
| 2004/0055891 A1 | 3/2004 | Pamula et al. |
| 2004/0058407 A1 | 3/2004 | Miller et al. |
| 2004/0058450 A1 | 3/2004 | Pamula et al. |
| 2004/0062685 A1 | 4/2004 | Norton et al. |
| 2004/0086870 A1 | 5/2004 | Tyvoll et al. |
| 2004/0091392 A1 | 5/2004 | McBride et al. |
| 2004/0101445 A1 | 5/2004 | Shvets et al. |
| 2004/0136876 A1 | 7/2004 | Fouillet et al. |
| 2004/0141884 A1 | 7/2004 | Unno et al. |
| 2004/0180346 A1 | 9/2004 | Anderson et al. |
| 2004/0209376 A1 | 10/2004 | Natan et al. |
| 2004/0211659 A1 | 10/2004 | Velev |
| 2004/0231987 A1 | 11/2004 | Sterling et al. |
| 2005/0014255 A1 | 1/2005 | Tang et al. |
| 2005/0036908 A1 | 2/2005 | Yu et al. |
| 2005/0037507 A1 | 2/2005 | Gauer |
| 2005/0048581 A1 | 3/2005 | Chiu et al. |
| 2005/0056569 A1 | 3/2005 | Yuan et al. |
| 2005/0064423 A1 | 3/2005 | Higuchi et al. |
| 2005/0084423 A1 | 4/2005 | Zarowitz et al. |
| 2005/0100675 A1 | 5/2005 | Mao et al. |
| 2005/0106742 A1 | 5/2005 | Wahl |
| 2005/0136551 A1 | 6/2005 | Mpock |
| 2005/0148042 A1 | 7/2005 | Prestwich et al. |
| 2005/0158755 A1 | 7/2005 | Lee et al. |
| 2005/0179746 A1 | 8/2005 | Roux et al. |
| 2005/0189049 A1 | 9/2005 | Ohno et al. |
| 2005/0227264 A1 | 10/2005 | Nobile et al. |
| 2005/0227349 A1 | 10/2005 | Kim et al. |
| 2005/0249636 A1 | 11/2005 | Tacklind et al. |
| 2005/0260686 A1 | 11/2005 | Watkins et al. |
| 2005/0282224 A1 | 12/2005 | Fouillet et al. |
| 2005/0287572 A1 | 12/2005 | Mathies et al. |
| 2006/0009705 A1 | 1/2006 | Brown |
| 2006/0021875 A1 | 2/2006 | Griffith et al. |
| 2006/0039823 A1 | 2/2006 | Yamakawa et al. |
| 2006/0040375 A1 | 2/2006 | Arney et al. |
| 2006/0054503 A1 | 3/2006 | Pamula et al. |
| 2006/0068450 A1 | 3/2006 | Combette et al. |
| 2006/0102477 A1 | 5/2006 | Vann et al. |
| 2006/0132927 A1 | 6/2006 | Yoon |
| 2006/0164490 A1 | 7/2006 | Kim et al. |
| 2006/0166261 A1 | 7/2006 | Higuchi et al. |
| 2006/0166262 A1 | 7/2006 | Higuchi et al. |
| 2006/0172336 A1 | 8/2006 | Higuchi et al. |
| 2006/0186048 A1 | 8/2006 | Tan |
| 2006/0194331 A1 | 8/2006 | Pamula et al. |
| 2006/0210443 A1 | 9/2006 | Stearns et al. |
| 2006/0231398 A1 | 10/2006 | Sarrut et al. |
| 2006/0254933 A1 | 11/2006 | Adachi et al. |
| 2007/0023292 A1 | 2/2007 | Kim et al. |
| 2007/0025879 A1 | 2/2007 | Vandergaw |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0075922 A1 | 4/2007 | Jessop |
| 2007/0086927 A1 | 4/2007 | Natarajan et al. |
| 2007/0141593 A1 | 6/2007 | Lee et al. |
| 2007/0178603 A1 | 8/2007 | Takii et al. |
| 2007/0179641 A1 | 8/2007 | Lucas et al. |
| 2007/0202538 A1 | 8/2007 | Glezer et al. |
| 2007/0207272 A1 | 9/2007 | Puri et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0264723 A1 | 11/2007 | Kim et al. |
| 2007/0267294 A1 | 11/2007 | Shenderov |
| 2007/0275415 A1 | 11/2007 | Srinivasan et al. |
| 2008/0003142 A1 | 1/2008 | Link et al. |
| 2008/0003588 A1 | 1/2008 | Hasson et al. |
| 2008/0006535 A1 | 1/2008 | Paik et al. |
| 2008/0023330 A1 | 1/2008 | Viovy |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0113081 A1 | 5/2008 | Hossainy et al. |
| 2008/0124252 A1 | 5/2008 | Marchand et al. |
| 2008/0138815 A1 | 6/2008 | Brown et al. |
| 2008/0142376 A1 | 6/2008 | Fouillet et al. |
| 2008/0151240 A1 | 6/2008 | Roth |
| 2008/0153091 A1 | 6/2008 | Brown et al. |
| 2008/0160525 A1 | 6/2008 | Brown et al. |
| 2008/0166793 A1 | 7/2008 | Beer et al. |
| 2008/0169184 A1 | 7/2008 | Brown et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171382 A1 | 7/2008 | Brown et al. |
| 2008/0210558 A1 | 9/2008 | Sauter-Starace et al. |
| 2008/0213766 A1 | 9/2008 | Brown et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0053726 A1 | 2/2009 | Owen et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |

(56) References Cited

U.S. PATENT DOCUMENTS

| | | |
|---|---|---|
| 2010/0213074 A1 | 8/2010 | Mousa et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0291578 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |
| 2013/0217113 A1 | 8/2013 | Srinivasan et al. |
| 2013/0217583 A1 | 8/2013 | Link et al. |
| 2013/0280131 A1 | 10/2013 | Handique et al. |
| 2016/0320378 A1 | 11/2016 | Pamula et al. |

FOREIGN PATENT DOCUMENTS

| | | |
|---|---|---|
| JP | 2006-276801 | 10/2006 |
| JP | 2006-317364 | 11/2006 |
| JP | 2006-329899 | 12/2006 |
| JP | 2006-329904 | 12/2006 |
| JP | 2008-096590 | 4/2008 |
| WO | 1998/022625 | 5/1998 |
| WO | 1999/015876 | 4/1999 |
| WO | 1999/017093 | 4/1999 |
| WO | 1999/054730 | 10/1999 |
| WO | 2000/069565 | 11/2000 |
| WO | 2000/073655 | 12/2000 |
| WO | 2001/007159 | 2/2001 |
| WO | 2003/045556 | 6/2003 |
| WO | 2003/069380 | 8/2003 |
| WO | 2004/011938 | 2/2004 |
| WO | 2004/027490 | 4/2004 |
| WO | 2004/029585 | 4/2004 |
| WO | 2004/030820 | 4/2004 |
| WO | 2004/073863 | 9/2004 |
| WO | 2005/047696 | 5/2005 |
| WO | 2005/069015 | 7/2005 |
| WO | 2006/003292 | 1/2006 |
| WO | 2006/013303 | 2/2006 |
| WO | 2006/026351 | 3/2006 |
| WO | 2006/070162 | 7/2006 |
| WO | 2006/081558 | 8/2006 |
| WO | 2006/085905 | 8/2006 |
| WO | 2006/124458 | 11/2006 |
| WO | 2006/127451 | 11/2006 |
| WO | 2006/129486 | 12/2006 |
| WO | 2006/132211 | 12/2006 |
| WO | 2006/134307 | 12/2006 |
| WO | 2006/138543 | 12/2006 |
| WO | 2007/003720 | 1/2007 |
| WO | 2007/012638 | 2/2007 |
| WO | 2007/033990 | 3/2007 |
| WO | 2007/048111 | 4/2007 |
| WO | 2007/094739 | 8/2007 |
| WO | 2007/120240 | 10/2007 |
| WO | 2007/120241 | 10/2007 |
| WO | 2007/123908 | 11/2007 |
| WO | 2008/051310 | 5/2008 |
| WO | 2008/055256 | 5/2008 |
| WO | 2008/068229 | 6/2008 |
| WO | 2008/091848 | 7/2008 |
| WO | 2008/098236 | 8/2008 |
| WO | 2008/101194 | 8/2008 |
| WO | 2008/106678 | 9/2008 |
| WO | 2008/109664 | 9/2008 |
| WO | 2008/112856 | 9/2008 |
| WO | 2008/116209 | 9/2008 |
| WO | 2008/116221 | 9/2008 |
| WO | 2008/118831 | 10/2008 |
| WO | 2008/124846 | 10/2008 |
| WO | 2008/131420 | 10/2008 |
| WO | 2008/134153 | 11/2008 |
| WO | 2009/002920 | 12/2008 |
| WO | 2009/003184 | 12/2008 |
| WO | 2009/011952 | 1/2009 |
| WO | 2009/021173 | 2/2009 |
| WO | 2009/021233 | 2/2009 |
| WO | 2009/026339 | 2/2009 |
| WO | 2009/029561 | 3/2009 |
| WO | 2009/032863 | 3/2009 |
| WO | 2009/052095 | 4/2009 |
| WO | 2009/052123 | 4/2009 |
| WO | 2009/052321 | 4/2009 |
| WO | 2009/052345 | 4/2009 |
| WO | 2009/052348 | 4/2009 |
| WO | 2009/076414 | 6/2009 |
| WO | 2009/086403 | 7/2009 |
| WO | 2009/111769 | 9/2009 |
| WO | 2009/135205 | 11/2009 |
| WO | 2009/137415 | 11/2009 |
| WO | 2009/140373 | 11/2009 |
| WO | 2009/140671 | 11/2009 |
| WO | 2010/004014 | 1/2010 |
| WO | 2010/006166 | 1/2010 |
| WO | 2010/009463 | 1/2010 |
| WO | 2010/019782 | 2/2010 |
| WO | 2010/027894 | 3/2010 |
| WO | 2010/042637 | 4/2010 |
| WO | 2010/077859 | 7/2010 |
| WO | 2011/002957 | 1/2011 |
| WO | 2011/020011 | 2/2011 |

OTHER PUBLICATIONS

Published Abstract from NIH Grant Project No. 1R43GM072155-01.
Published Abstract from NIH Grant Project No. 2R44DK066956-02.
Published Abstract from NIH Grant Project No. HG003076.
Published Abstract from NIGH Grant No. 5U01A1066590-02 titled "Microfluidic PCR Platform to Detect Microbial DNA", project start date of Jul. 5, 2005.
PCT International Search Report and Written Opinion for PCT/US2009/059868, dated May 19, 2010.
PCT International Preliminary Report on Patentability for PCT/US2009/059868, dated Apr. 12, 2011.
PCT International Preliminary Report on Patentability for PCT/US2006/047486, dated Aug. 15, 2010.
PCT International Search Report and Written Opinion for PCT/US2007/009379, dated Aug. 18, 2008.
PCT International Search Report and Written Opinion for PCT/US2005/030247, dated Dec. 20, 2005.

(56) References Cited

OTHER PUBLICATIONS

PCT International Preliminary Report on Patentability for PCT/US2005/030247, dated Feb. 28, 2007.
PCT International Search Report and Written Opinion for PCT/US2007/011298, dated Jun. 25, 2008.
PCT International Search Report and Written Opinion for PCT/US2008/080264, dated Jun. 2, 2009.
PCT International Preliminary Report on Patentability for PCT/US2008/080264, dated Apr. 20, 2010.
PCT International Search Report and Written Opinion for PCT/US2006/047481, dated May 5, 2008.
PCT International Search Report and Written Opinion for PCT/US2006/047486, dated May 2, 2008.
Agah, A., "DNA Analysis Chip by Electrowetting Actuation", Stanford Nanofabrication Facility, 2002.
Al-Rubeai, et al., "The effect of Pluronic F-68 on hybridoma cells in continuous culture", Applied Microbiol. Biotechnol., 1992, 44-45.
Barbulovic-Nad, et al., "Digital microfluidics for cell-based assays", Lab on a chip, vol. 8, Apr. 2008, 519-526.
Batchelder, et al., "Dielectrophoretic manipulator", Review of Scientific Instruments, vol. 54 ., 1983, 300-302.
Baviere, et al., "Dynamics of droplet transport induced by electrowetting actuation", Microfluidics and Nanofluidics, vol. 4, May 2007, pp. 287-294.
Bhansali, et al., "Resolving chemical/bio-compatibility in microfluidic MEMS systems", SPIE Conference on Microfluidic Devices and Systems II, vol. 3877., 1999, 101-109.
Binks, "Wetting: theory and experiment", Current Opinion in Colloids and Interface Science, vol. 6, No. 1, 2001, 17-21.
Brady, "Electrowetting for DNA Sequencing on Chip", NNIN REU Research Accomplishments, 2004, 26-27.
Brassard, et al., "Water-oil core-shell droplets for electrowetting-based digital microfluidic devices", Lab on a chip, vol. 8, 2008, 1342-1349.
Chakrabarty, , "Automated Design of Microfluidics-Based Biochips: connecting Biochemistry of Electronics CAD", IEEE International Conference on Computer Design, San Jose, CA, Oct. 1-4, 2006, 93-100.
Chakrabarty, et al., "Design Automation Challenges for Microfluidics-Based Biochips", DTIP of MEMS & MOEMS, Montreux, Switzerland, Jun. 1-3, 2005.
Chakrabarty, et al., "Design Automation for Microfluidics-Based Biochips", ACM Journal on Engineering Technologies in Computing Systems , 1(3), Oct. 2005, pp. 186-223.
Chakrabarty, , "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005, 39 pages.
Chamberlain, et al., "Deletion screening of Duchenne musular dystrophy locus via multiplex DNA amplification", Nuc. Acid. Res. 16, 1988, pp. 11141-11156.
Chang, et al., "Integrated polymerase chain reaction chips utilizing digital microfluidics", Biomedical Microdevices, vol. 8, May 20, 2006, 215-225.
Chatterjee, et al., "Droplet-based microfluidics with nonaqueous solvents and solutions", Lab on a Chip, vol. 6., Feb. 2006, 199-206.
Chatterjee, et al., "Lab on a Chip Applications with a Digital Microfluidic Platform", UCLA Dissertation, UMI Microform No. 3342975, 2008, 186 pages.
Chen, Q. et al., "Development of Mesoscale Actuator Device with Micro Interlocking Mechanism", J. Intelligent Material Systems and Structures, vol. 9, No. 4, Jun. 1998, pp. 449-457.
Chen, Q. et al., "Mesoscale Actuator Device with Micro Interlocking Mechanism", Proc. IEEE Micro Electro Mechanical Systems Workshop, Heidelberg, Germany, Jan. 1998, pp. 384-389.
Chen, Q. et al., "Mesoscale Actuator Device: Micro Interlocking Mechanism to Transfer Macro Load", Sensors and Actuators, vol. 73, Issues 1-2, Mar. 1999, pp. 30-36.

Chin, et al., "Lab-on-a-chip devices for global health past studies and future opportunities", Lab on a Chip, vol. 7, Jan. 2007, pp. 41-57.
Chiou, et al., "Light actuation of liquid by optoelectrowetting", Sensors and Actuators A: Physical, vol. 104, May 2003, 222-228.
Cho, et al., "Concentration and binary separation of micro particles for droplet-based digital microfludics", Lab Chip, vol. 7, 2007, 490-498.
Cho, et al., "Creating, Transporting, Cutting, and Merging Liquid Droplets by Electrowetting-Based Actuation for Digital Microfluidic Circuits", Journal of Microelectromechanical Systems, vol. 12, No. 1, Feb. 2003, 70-80.
Cho, et al., "Splitting a Liquid Droplet for Electrowetting-Based Microfluidics", Proceedings of 2001 ASME International Mechanical Engineering Congress and Exposition, IMECE2001/MEMS-23830, New York, NY, Nov. 11-16, 2001, 7 pages.
Colgate, et al., "An Investigation of Electrowetting-based Microactuation", Journal of Vacuum Science & Technology A—Vacuume Surfaces and Films, vol. 8 (4), Jul.-Aug. 1990, 3625-3633.
Cooney, et al., "Electrowetting droplet microfluidics on a single planar surface", Microfluidics and Nanofluidics,vol. 2., Mar. 2006, 435-446.
Cotten, et al., "Digital Microfluidics: a novel platform for multiplexed detection of lysosomal storage diseases", Abstract # 3747.9. Pediatric Academic Society Conference, 2008.
Delattre, Movie in news on TF1 (at 12'37" Cyril Delattre), http://videos.tf1.fr/jt-we/zoom-sur-grenoble-6071525.html, 2009, (English translation of audio), 2009.
Delattre, Movie in talk show "C Dans l'air" (at 24" Cyril Delattre), http://www.france5.fr/c-dans-l-air/sante/bientot-vous-ne-serez-plus-malade-31721, 2009, (English translation of audio), 2009.
Delattre, Movie on Web TV—Cite des sciences (at 3'26" Cyril Delattre), http://www.universcience.tv/videolaboratoire-de-poche-793.html, 2009, (English translation of audio), 2009.
Delattre, et al., "Towards an industrial fabrication process for electrowetting chip using standard MEMS Technology", µTAS2008, San Diego; poster presented, Oct. 15, 2008.
Delattre, et al., "Towards an industrial fabrication process for electrowetting chip using standard MEMS Technology", µTAS2008, San Diego; Abstract in proceedings, Oct. 13-16, 2008, 1696-1698.
Dewey, et al., "Visual modeling and design of microelectromechanical system transducers", Microelectronics Journal, vol. 32, Apr. 2001, 373-381.
Ding, "System level architectural optimization of semi-reconfigurable micro fluidic system", M.S. Thesis, Duke University Dept of Electrical Engineering, 2000.
Dorfman, et al., "Contamination-Free Continuouse Flow Microfluidic Polymerase Chain Reaction for Quantitative and Clinical Applications", Analytical Chemistry 77, 2005, 3700-3704.
Dubois, et al., "Ionic Liquid Droplet as e-Microreactor", Analytical Chemistry, vol. 78, 2006, 4909-4917.
Fair, et al., "A Micro-Watt Metal-Insulator-Solution-Transport (MIST) Device for Scalable Digital Bio-Microfluidic Systems", IEEE IEDM Technical Digest, 2001, 16.4.1-4.
Fair, et al., "Advances in droplet-based bio lab-on-a-chip", BioChips, Boston, 2003.
Fair, et al., "Bead-Based and Solution-Based Assays Performed on a Digital Microfluidic Platform", Biomedical Engineering Society (BMES) Fall Meeting, Baltimore, MD, Oct. 1, 2005.
Fair, "Biomedical Applications of Electrowetting Systems", 5th International Electrowetting Meeting, Rochester, NY, May 31, 2006.
Fair, et al., "Chemical and biological pathogen detection in a digital microfluidic platform", DARPA Workshop on Microfluidic Analyzers for DoD and National Security Applications, Keystone, CO, 2006.
Fair, "Digital microfluidics: is a true lab-on-a-chip possible?", Microfluid Nanofluid, vol. 3, Mar. 8, 2007, 245-281.
Fair, "Droplet-based microfluidic genome sequencing", NHGRI PI's meeting, Boston, 2005.
Fair, et al., "Electrowetting-based On-Chip Sample Processing for Integrated Microfluidics", IEEE Inter. Electron Devices Meeting (IEDM), 2003, 32.5.1-32.5.4.

(56) References Cited

OTHER PUBLICATIONS

Fair, et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fair, "Scaling of Digital Microfluidic Devices for Picoliter Applications", The 6th International Electrowetting Meeting, Aug. 20-22, 2008, p. 14.
Fan, Shih-Kang, "Digital Microfluidics by Cross-Reference EWOD Actuation: Principle, Device and System", PhD Dissertation, University of California Dept. of Mechanical Engineering, 2003.
Fouillet, "Bio-Protocol Integration in Digital Microfluidic Chips", The 6th International Electrowetting Meeting, Aug. 20-22, 2008, p. 15.
Fouillet, et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Fouillet, et al., "Digital microfluidic design and optimization of classic and new fludic functions for lab on a chip systems", Microfluid Nanofluid 4, 2008, 159-165.
Fowler, "Lab-on-a-Chip Technology May Present New ESD Challenges", Electrostatic Discharge (ESD) Journal. Retrieved on Apr. 18, 2008 from:http://www.esdjournal.com/articles/labchip/Lab.htm., Mar. 2002.
Furdui, et al., "Immunomagnetic T cell recapture from blood for PCR analysis using microfluidic systems", Lab Chip vol. 4, 2004, 614-618.
Garrell, et al., "Preventing Biomolecular Absorption in Electrowetting-Based Biofluidic Chips", Analytical Chemistry, vol. 75, Oct. 2003, 5097-5102.
Gijs, Mam "Magnetic bead handling on-chip:new opportunities for analytical applications", Microfluidics and Nanofluidics, vol. 1, Oct. 2, 2004, 22-40.
Gong, et al., "Direct-referencing two-dimensional-array digital microfluidics using multi-layer printed circuit board", Journal of Microelectromechanical Systems, vol. 17, Apr. 2008, 257-264.
Guttenberg, et al., "Planar chip devices for PCR and hybridization with surface acoustic wave pump", Lab on a chip, vol. 5, Mar. 2005, 12617-22.
Hua, et al., "Rapid Detection of Methicillin-Resistant *Staphylococcus aureus* (MRSA) Using Digital Microfluidics", 12th Intl Conference on Miniaturized Systems for Chemistry and Life Sciences, Proc. μTAS, Oct. 12-16, 2008.
Huang, et al., "MEMS-based sample preparation for molecular diagnostics", Analytical and Bioanalytical Chemistry, vol. 372, 2002, 49-65.
Jary, et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.
Jary, et al., "SmartDrop, Microfluidics for Biology", Forum 4i 2009, Grenoble, France; Flyer distributed at booth, May 14, 2009.
Jones, et al., "Dielectrophoretic liquid actuation and nanodroplet formation", J. Appl. Phys., vol. 89, No. 2, Jan. 2001, 1441-1448.
Jun, T.K. et al., "Valveless Pumping using Traversing Vapor Bubbles in Microchannels", J. Applied Physics, vol. 83, No. 11, Jun. 1998, pp. 5658-5664.
Kajiyama, et al., "Enhancement of Thermostability of Firefly Luciferase from Luciola lateralis by a Single Amino Acid Substitution", Biosci. Biotech. Biochem., vol. 58 (6), 1994, 1170-1171.
Kim, C.-J. et al., "MEMS Devices Based on the Use of Surface Tension", Proc. Int. Semiconductor Device Research Symposium (ISDRS'99), Charlottesville, VA, Dec. 1999, pp. 481-484.
Kim, C.-J. "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim, C.-J. et al., "Micromachines Driven by Surface Tension", AIAA 99-3800, 30th AIAA Fluid Dynamics Conference, Norfolk, VA, (Invited lecture), Jun. 1999, pp. 1-6.
Kleinert, et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.
Koyama, et al., "Evaluatin of magnetic Beads Agitation Performance Operated by Multi-Layered Flat Coils", Solid-State Sensors, Actuators and Microsystems Conference, 2007. Transducers 2007. International, IEEE, Piscataway, NJ, USA, Jun. 10, 2007, pp. 2385-2388.
Lee, et al., "Electrowetting and electrowetting-on-dielectric for microscale liquid handling", Sensors and Actuators, vol. 95, 2002, 259-268.
Lee, et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee, J. et al., "Liquid Micromotor Driven by Continuous Electrowetting", Proc. IEEE Micro Electro Mechanical Systems Workshop, Heidelberg, Germany, Jan. 1998, pp. 538-543.
Lee, J. et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.
Lehmann, et al., "Droplet-Based DNA Purification in a Magnetic Lab-on-a-Chip", Angewandte Chemie, vol. 45., 2006, 3062-3067.
Lehmann, et al., "Two-dimensional magnetic manipulation of microdroplets on a chip as a platform for bioanalytical applications", Sensors and Actuators B, vol. 117, 2006, 457-463.
Liu, et al., "Effect of Non-Ionic Surfactants on the Formation of DNA/Emulsion Complexes and Emulsion-Medicated Gene Transfer", Pharmaceutical Research, vol. 13, No. 11, 1996, 1642-1646.
Locascio, et al., "Polymer microfluidic devices", Talanta, vol. 56, Feb. 2002, 267-287.
Luan, et al., "Integrated Optical Sensor in a Digital Microfluidic Platform", IEEE Sensors Journal, vol. 8, May 2008, 628-635.
Luk, et al., "Pluronic additives: a solution to sticky problems in digital microfluidics", Langmuir: the ACS journal of surfaces and colloids, vol. 24, Jun. 2008, 6382-6389.
Madou, et al., "Lab on a CD", Annual Review of Biomedical Engineering, vol. 8, 2006, 601-628.
Malic, et al., "Biochip fuctionalization using electrowetting-on-dielectric digital microfluidics for surface plasmon resonance imaging detection of DNA hybridization", Biosensors & Bioelectronics, vol. 24, Mar. 2009, 2218-2224.
Manz, et al., "Miniaturized Total Chemical Analysis Systems: a Novel Concept for Chemical Sensing", Sensors and Actuators B: Chemical, 1990, 244-248.
Marchand, et al., "Organic Synthesis in Soft Wall-Free Microreactors: Real-Time Monitoring of Fluorogenic Reactions", Analytical Chemistry, vol. 80, Jul. 2, 2008, 6051-6055.
Margulies, et al., "Genome sequencing in microfabricated high-density picolitre reactors," Nature, vol. 437, 376-380 and Supplemental Materials, 2005.
Mariella, et al., "Sample preparation: the weak link in microfluidics-based biodetection", Biomedical Microdevices, vol. 10, Dec. 2008, 777-784.
McDonald, et al., "Fabrication of Microfluidic systems in poly (dimethylsiloxane)", Electrophoresis, vol. 21, 2000, 27-40.
Miller, et al., "A Digital Microfluidic Approach to Homogeneous Enzyme Assays", Analytical Chemistry, vol. 80, 2008, 1614-1619.
Millington, et al., "Digital Microfluidics: a novel platform for multiplexed detection of LSDs with potential for newborn screening", Association of Public Health Laboratories Annual Conference, San Antonio, TX, Nov. 4, 2008.
Millington, et al., "Digital Microfluidics: A Novel Platform for Multiplexing Assays Used in Newborn Screening", Proceedings of the 7th International and Latin American Congress. Oral Presentations. Rev Invest Clin; vol. 61 (Supl. 1), 2009, 21-33.

(56) References Cited

OTHER PUBLICATIONS

MIT Tech Review, "Chip mixes droplets faster", MIT Technology Review. Retrieved on Apr. 18, 2008 from:http://www.trnmag.com/Stories/2003/102203/Chip_mixes_droplets_faster_Brief_102203.html., Oct. 2003.
Mohanty, et al., "Two Dimensional Micro Gel Electrophoresis Device with Integrated Removeable Capillary Insert (Rci) for Macro-Micro Interface and Post Separation Sample Manipulation", American Electrophoresis Society (AES) Annual Meeting, Nov. 2, 2005.
Moon, "Electrowetting-on-dielectric microfluidics: Modeling, physics, and MALDI application", Dissertation, University of California, Los Angeles, Aug. 2005.
Moon, et al., "Low voltage electrowetting-on-dielectric", Journal of Applied Physics, vol. 92 (7), Oct. 1, 2002, 4080-4087.
Mousa, et al., "Droplet-scale estrogen assays in breast tissue, blood, and serum", Science Translational Medicine, vol. 1, Issue 1, 1ra2, Oct. 7, 2009, 1-6.
Mugele, et al., "Electrowetting: from basics to applications", Journal of Physics: Condensed Matter, vol. 17, Jul. 2005, R705-R774.
Mukhopadhyay, R. et al., "Microfluidic: on the slope of enlightement", Analytical Chemstry, vol. 81, Jun. 2009, 4169-4173.
Noderer, et al., "DNA pyrosequencing using microfluidic chips", NNIN REU Research Accomplishments, 2005, 96-97.
Nyren, et al., "Enzymatic Method for Continuous Monitoring of Inorganic Pyrophosphate Synthesis", Anal. Biochem., vol. 151, Issue 2, Dec. 1985, 504-509.
Paik, et al., "A digital-microfluidic approach to chip cooling", IEEE Design & Test of Computers, vol. 25, Jul. 2008, 372-381.
Paik, et al., "Adaptive Cooling of Integrated Circuits Using Digital Microfluidics", accepted for publication in IEEE Transactions on VLSI Systems, and Artech House, Norwood, MA, 2007.
Paik, et al., "Adaptive cooling of integrated circuits using digital microfluidics", IEEE Transactions on VLSI, vol. 16, No. 4, 2008, 432-443.
Paik, "Adaptive Hot-Spot Cooling of Integrated Circuits Using Digital Microfluidics", Dissertation, Dept. of Electrical and Computer Engineering, Duke University, Apr. 25, 2006, 1-188.
Paik, et al., "Adaptive hot-spot cooling of integrated circuits using digital microfluidics", Proceedings, ASME International Mechanical Engineering Congress and Exposition, Orlando, Florida, USA. IMECE2005-81081, Nov. 5-11, 2005, 1-6.
Paik, et al., "Coplanar Digital Microfluidics Using Standard Printed Circuit Board Processes", 9th International Conference on Miniaturized Systems for Chemistry and Life Sciences (MicroTAS), Boston, MA; Poster, Oct. 2005.
Paik, et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik, et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik, et al., "Electrowetting-based droplet mixers for microfluidic systems", Lab on a Chip (LOC), vol. 3. (more mixing videos available, along with the article, at LOC's website), 2003, 28-33.
Paik, et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.
Paik, et al., "Programmable flow-through real-time PCR using digital microfluidics", Proc. Micro Total Analysis Systems (µTAS), Handout, 2007.
Paik, et al., "Programmable flow-through real-time PCR using digital microfluidics", Proc. Micro Total Analysis Systems (µTAS), Poster, 2007.
Paik, et al., "Rapid Droplet Mixers for Digital Microfluidic Systems", Masters Thesis, Duke Graduate School., 2002, 1-82.
Paik, et al., "Rapid droplet mixers for digital microfluidic systems", Lab on a Chip, vol. 3. (More mixing videos available, along with the article, at LOC's website.), 2003, 253-259.
Paik, et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamme, "Magnetism and microfluidics", Lab on a Chip (LOC), vol. 6., 2006, 24-38.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula, et al., "A droplet-based lab-on-a-chip for colorimetric detection of nitroaromatic explosives", Proceedings of Micro Electro Mechanical Systems, 2005, 722-725.
Pamula, et al., "Cooling of integrated circuits using droplet-based microfluidics", Proc. ACM Great Lakes Symposium on VLSI, Apr. 2003, 84-87.
Pamula, et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula, et al., "Digital Microfluidics Platform for Lab-on-a-chip applications", Duke University Annual Post Doctoral Research Day, 2002.
Pamula, et al., Microfluidic electrowetting-based droplet mixing, Department of Electrical Engineering, Duke University, 2002.
Pamula, et al., "Microfluidic electrowetting-based droplet mixing", IEEE, 2002, 8-10.
Pamula, "Sample Preparation and Processing using Magnetic Beads on a Digital Microfluidic Platform", Cambridge Healthtech Institute's Genomic Tools & Technologies Summit, San Francisco, CA, Jun. 9-10, 2009.
Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.
Pamula and Chakrabarty (Co-Chair, "Digital Microfluidics for Lab-on-a-Chip Applications", "Emerging CAD Challenges for Biochip Design" Workshop, Conference on Design, Automation, and Test in Europe (DATE), Munich, Germany, Advance Programme, 2006, pp. 85-87.
Patch, "Chip juggles droplets", Technology Research News, Retrieved on Apr. 18, 2008 from: http://www.trnmag.com/Stories/2002/090402/Chip_juggles_droplets_090402.html, Sep. 4-11, 2002.
Pinho, et al., "Haemopoietic progenitors in the adult mouse omentum: permanent production of B lymphocytes and monocytes", Cell Tissue Res., vol. 319, No. 1, Jan. 2005, 91-102.
Pipper, et al., "Clockwork PCR Including Sample Preparation", Angew. Chem. Int. Ed., vol. 47, 2008, 3900-3904.
Pollack, et al., "Electrowetting-Based Actuation of Droplets for Integrated Microfluidics", Lab on a Chip (LOC), vol. 2, 2002, 96-101.
Pollack, et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack, et al., "Electrowetting-Based Microfluidics for High-Throughput Screening", smallTalk 2001 Conference Program Abstract, San Diego, Aug. 27-31, 2001, 149.
Pollack, et al., "Investigation of electrowetting-based microfluidics for real-time PCR applications", Proc. of Utas 2003 7th Int'l Conference on Micro Total Analysis Systems (µTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Poliski, Making materials fit the future: accommodating relentless technological requirements means researchers much recreate and

(56) References Cited

OTHER PUBLICATIONS reconfigure materials, frequently challenging established laws of physics, while keeping an eye on Moore's law, R&D Magazine Conference, Dec. 2001.
Popular Mechanics, "Laboratory on a Chip", Popular Mechanics—Tech Watch, Retrieved on Apr. 18, 2008 from: http://www.ee.duke.edu/research/microfluidics/images/PopMechArticle.JPG, Mar. 2002.
Poulos, et al., "Electrowetting on dielectric-based microfluidics for integrated lipid bilayer formation and measurement", Applied Physics Letters, vol. 95, 2009, 013706.
Raccurt, et al., "On the influence of surfactants in electrowetting systems", J. Micromech. Microeng., vol. 17, 2007, 2217-2223.
Raj, et al., "Composite Dielectrics and Surfactants for Low Voltage Electrowetting Devices", University/Government/Industry Micro/Nano Symposium, vol. 17, Jul. 13-16, 2008, 187-190.
Ren, et al., "Automated electrowetting-based droplet dispensing with good reproducibility", Proc. Micro Total Analysis Systems (µTAS), 7th Int. Conf.on Miniaturized Chem and Biochem Analysis Systems, Squaw Valley, CA, Oct. 5-9, 2003, 993-996.
Ren, et al., "Automated on-chip droplet dispensing with volume control by electro-wetting actuation and capacitance metering", Sensors and Actuators B: Chemical, vol. 98, Mar. 2004, 319-327.
Ren, et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren, et al., "Dynamics of electro-wetting droplet transport", Sensors and Actuators B (Chemical), vol. B87, No. 1, Nov. 15, 2002, 201-206.
Ren, et al., "Micro/Nano Liter Droplet Formation and Dispensing by Capacitance Metering and Electrowetting Actuation", IEEE-NANO, 2002, 369-372.
Rival, et al., "Towards Single Cells Gene Expression on EWOD Lab on Chip", ESONN, Grenoble, France; Poster presented, Aug. 26, 2008.
Rival, et al., "Towards single cells gene expression on EWOD lab on chip", ESONN, Grenoble, France, abstract in proceedings, Aug. 2008.
Rival, et al., "Towards single cells gene expression preparation and analysis on EWOD lab on chip", Nanobio Europe 2009, Poster distributed at conference, Jun. 16-18, 2009.
Rival, et al., "Towards single cells gene expression preparation and analysis on EWOD lab on chip", Nanobio Europe 2009, Abstract in proceedings, Jun. 16-18, 2009.
Rival, et al., "Towards single cells gene expression preparation and analysis on ewod lab on chip", Lab on Chip Europe 2009 poster distributed at Conference, May 19-20, 2009.
Rival, et al., "Towards single cells gene expression preparation and analysis on ewod lab on chip", Lab on Chip Europe 2009, Abstract in proceedings, May 19-20, 2009.
Rouse, et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Roux, et al., "3D droplet displacement in microfluidic systems by electrostatic actuation", Sensors and Actuators A, vol. 134, Issue 2, Mar. 15, 2007, 486-493.
Russom, et al., "Pyrosequencing in a Microfluidic Flow-Through Device", Anal. Chem. vol. 77, 2005, 7505-7511.
Schwartz, et al., "Dielectrophoretic approaches to sample preparation and analysis", The University of Texas, Dissertation, Dec. 2001.
Schwartz, et al., "Droplet-based chemistry on programmable microchip", Lab on a Chip, vol. 4, No. 1, 2002, 11-17.
Shah, et al., "EWOD-driven droplet microfluidic device integrated with optoelectronic tweezers as an automated platform for cellular isolation and analysis", Lab on a Chip, vol. 9, Jun. 2009, 1732-1739.
Sherman, F. et al., "Flow Control by Using High-Aspect-Ratio, In-Plane Microactuators", Sensors and Actuators, vol. 73, 1999, pp. 169-175.
Sherman, F. et al., "In-Plane Microactuator for Fluid Control Application", Proc. IEEE Micro Electro Mechanical Systems Workshop, Heidelberg, Germany, Jan. 1998, pp. 454-459.
Shikida, et al., "Using wetability and interfacial tension to handle droplets of magnetic beads in a micro-chemical-analysis system", Sensors and Actuators, vol. 113, 2006, 563-569.
Sista, et al., "96-Immunoassay Digital Microfluidic Multiwell Plate", Proc. µTAS, Oct. 12-16, 2008.
Sista, "Development of a Digital Microfluidic Lab-on-a-Chip for Automated Immunoassays with Magnetically Responsive Beads", PhD Thesis, Department of Chemical Engineering, Florida State University, 2007.
Sista, et al., "Development of a Digital Microfluidic Platform for Point of Care Testing," Lab on a Chip, vol. 8, Dec. 2008, First published as an Advance Article on the web, Nov. 5, 2008, 2091-2104.
Sista, et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista, et al., "Spatial multiplexing of immunoassays for small-volume samples", 10th PI Meeting IMAT, Bethesda, 2009.
Squires, et al., "Microfluidics:Fluid physics at the nanoliter scale", Reviews of Modern Physics, vol. 77, 2005, 977-1026.
Srinivasan, et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan, et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Dissertation submitted in partial fulfillment of the requirements for the degree of Doctor of Philosophy in the Department of Electrical and Computer Engineering in the Graduate School of Duke University, 2005, 136 pages.
Srinivasan, et al., "An integrated digital microfluidic lab-on-a-chip for clinical diagnostics on human physiological fluids", Lab on a Chip, vol. 4, 2004, 310-315.
Srinivasan, et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan, et al., "Digital Microfluidic Lab-on-a-Chip for Protein Crystallization", The 82nd ACS Colloid and Surface Science Symposium, Abstract Book, 2008, 269-321.
Srinivasan, et al., "Digital Microfluidics: a novel platform for multiplexed detection of lysosomal storage diseases for newborn screening", AACC Oak Ridge Conference Abstracts, Clinical Chemistry, vol. 54, Apr. 17-18, 2008, 1934.
Srinivasan, et al., "Droplet-based microfluidic lab-on-a-chip for glucose detection", Analytica Chimica Acta, vol. 507, No. 1, 2004, 145-150.
Srinivasan, et al., "Low cost digital microfluidic platform for protein crystallization", Enabling Technologies for Structural Biology, NIGMS Workshop, Bethesda, MD., Mar. 4-6, 2009, J-23.
Srinivasan, et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan, et al., "Scalable Macromodels for Microelectromechanical Systems", Technical Proc. 2001 Int. Conf. on Modeling and Simulation of Microsystems, 2001, 72-75.
Su, et al., "Testing of droplet-based microelectrofluidic systems", Proc. IEEE International Test Conference, 2003, 1192-1200.
Su, et al., "Yield Enhancement of Digital Microfluidics-Based Biochips Using Space Redundancy and Local Reconfiguration", Proc. Design, Automation and Test in Europe Conf., IEEE, 2005, 1196-1201.
Sudarsan, et al., "Printed circuit technology for fabrication of plastic based microfluidic devices", Analytical Chemistry vol. 76, No. 11, Jun. 1, 2004, Previously published on-line, May 2004, 3229-3235.

(56) References Cited

OTHER PUBLICATIONS

Taira, et al., "Immobilization of Single-Stranded DNA by Self-Assembled Polymer on Gold Substrate for a DNA Chip", Biotechnology and Bioengineering, vol. 89, Issue 7, Mar. 30, 2005, 835-838.
Taniguchi, et al., "Chemical reactions in microdroplets by electrostatic manipulation of droplets in liquid media", Lab on a Chip, vol. 2, No. 2, 2002, 19-23.
Teh, et al., "Droplet microfluidics", Lab on a chip, vol. 8, Feb. 2008, 198-220.
Terry, et al., "A Gas Chromatographic Air Analyzer Fabricated on a Silicon Wafer", IEEE Transactions on Electron Devices, vol. ED-26, 1979, 1880-1886.
Thwar, et al., "DNA sequencing using digital microfluidics", Poster 42, 41st AACC's Annual Oak Ridge Conference Abstracts, Clinical Chemistry, vol. 55, No. 10, Oct. 2009, 1891.
Torkkeli, "Droplet microfluidics on a planar surface", Doctoral Dissertation, Department of Electrical Engineering, Helsinki University of Technology, Oct. 3, 2003.
Tsuchiya, et al., "On-chip polymerase chain reaction microdevice employing a magnetic droplet-manipulation system", Sensors and Actuators B, vol. 130, Oct. 18, 2007, 583-588.
Tuckerman, et al., "High-Performance Heat Sinking for VLSI", IEEE Electron Device Letters, 1981, 126-129.
Verpoorte, "Beads and chips: new recipes for analysis", Lab on a Chip (LOC), vol. 3., 2003, 60N-68N.
Wang, et al., "Droplet-based micro oscillating-flow PCR chip", J. Micromechanics and Microengineering, vol. 15, 2005, 1369-1377.
Wang, et al., "Efficient in-droplet separation of magnetic particles for digital microfluidics", Journal of Micromechanics and Microengineering, vol. 17, 2007, 2148-2156.
Washizu, "Electrostatic Actuation of Liquid Droplets for Micro-Reactor Applications", IEEE Industry Applications Society Annual Meeting, Oct. 5-9, 1997, 1867-1873.
Weaver, "Application of Magnetic Microspheres for Pyrosequencing on a Digital Microfluidic Platform", Department of Electrical and Computer Engineering, Duke University, Web publication, Aug. 29, 2005.
Weber, et al., "Specific Blood Purification by Means of Antibody-Conjugated Magnetic Microspheres", Centre for Biomedical Technology, Austria, Scientific and Clinical Applications of Magnetic Carriers, 1997.
Wego, et al., "Fluidic microsystems based on printed circuit board technology", Journal of Micromechanics and Microengineering, vol. 11, No. 5, Sep. 2001, 528-531.
Wheeler, et al., "Electrowetting-Based Microfluidics for Analysis of Peptides and Proteins by Matrix-Assisted Laser Desportion/Ionization Mass Spectrometry", Anal. Chem. 76, 2004, 4833-4838.
Wheeler, et al., "Electrowetting-on-dielectric for analysis of peptides and proteins by matrix assisted laser desorption / ionization mass spectrometry", Solid-State Sensor, Actuator and Microsystems Workshop publication, Jun. 6-10, 2004, 402-403.
Wheeler, "Putting Electrowetting to Work", Science, vol. 322, No. 5901, Oct. 24, 2008, 539-540.
Whitesides, "The origins and future of microfluidics", Nature, vol. 442, 2006, 368-373.
Xu, et al., "A Cross-Referencing-Based Droplet Manipulation Method for High-Throughput and Pin-Constrained Digital Microfluidic Arrays", Proceedings of conference on Design, Automation and Test in Europe, Apr. 2007.
Xu, et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.
Xu, et al., "Automated solution preparation on a digital microfluidic lab-on-chip", PSI Bottlenecks Workshop, 2008.
Xu, et al., "Automated, Accurate and Inexpensive Solution-Preparation on a Digital Microfluidic Biochip", Proc. IEEE Biomedical Circuits and Systems Conference (BioCAS), 2008, 301-304.
Xu, et al., "Defect-Aware Synthesis of Droplet-Based Microfluidic Biochips", IEEE, 20th International Conference on VLSI Design, 2007.
Xu, et al., "Design and Optimization of a Digital Microfluidic Biochip for Protein Crystallization", Proc. IEEE/ACM International Conference on Computer-Aided Design (ICCAD), Nov. 2008, 297-301.
Xu, et al., "Digital Microfluidic Biochip Design for Protein Crystallization", IEEE-NIH Life Science Systems and Applications Workshop, LISA, Bethesda, MD, Nov. 8-9, 2007, 140-143.
Xu, et al., "Droplet-Trace-Based Array Partitioning and a Pin Assignment Algorithm for the Automated Design of Digital Microfluidic Biochips", CODES, 2006, 112-117.
Xu, et al., "Integrated Droplet Routing in the Synthesis of Microfluidic Biochips", IEEE, 2007, 948-953.
Xu, et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu, et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Yao, D.-J. et al., "Spot Cooling Using Thermoelectric Microcooler", Proc. 18th Int. Thermoelectric Conf, Baltimore, MD, Aug. 1999, pp. 256-259.
Yi, et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi, et al., "Characterization of electrowetting actuation on addressable single-side coplanar electrodes", Journal of Micromechanics and Microengineering, vol. 16.,Oct. 2006 http://dx.doi.org/10.1088/0960-1317/16/10/018, published online at stacks.iop.org/JMM/16/2053, Aug. 25, 2006, 2053-2059.
Yi, et al., "EWOD Actuation with Electrode-Free Cover Plate", Digest of Tech. papers,13th International Conference on Solid-State Sensors, Actuators and Microsystems (Transducers '05), Seoul, Korea, Jun. 5-9, 2005, 89-92.
Yi, et al., "Geometric surface modification of nozzles for complete transfer of liquid drops", Solid-State Sensor, Actuator and Microsystems Workshop, Hilton Head Island, South Carolina, Jun. 6-10, 2004, 164-167.
Yi, et al., "Microfluidics technology for manipulation and analysis of biological cells", Analytica Chimica Acta, vol. 560, 2006, 1-23.
Yi, "Soft Printing of Biofluids for Micro-arrays: Concept, Principle, Fabrication, and Demonstration", Ph.D. dissertation, UCLA, 2004.
Yi, et al., "Soft Printing of Droplets Digitized by Electrowetting", Transducers 12th Int'l Conf. on Solid State Sensors, Actuators and Microsystems, Boston, Jun. 8-12, 2003, 1804-1807.
Yi, et al., "Soft Printing of Droplets Pre-Metered by Electrowetting", Sensors and Actuators A: Physical, vol. 114, Jan. 2004, 347-354.
Zeng, et al., "Actuation and Control of Droplets by Using Electrowetting-on-Dielectrc", Chin. Phys. Lett. vol. 21, No. 9, 2004, 1851-1854.
Zhao, et al., "Droplet Manipulation and Microparticle Sampling on Perforated Microfilter Membranes", J. Micromech. Microeng., vol. 18, 2008, 1-11.
Zhao, et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.
Zhao, et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.
Zhao, et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

600 ⟶

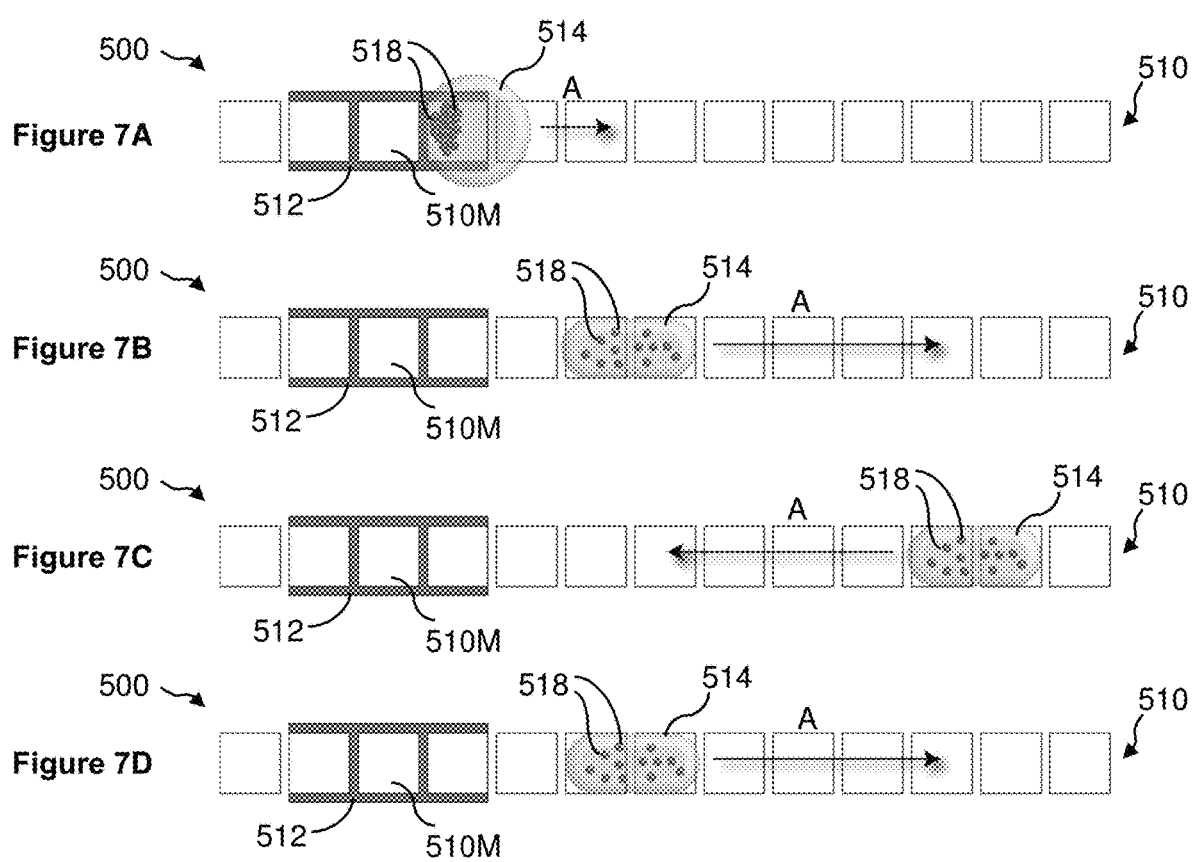

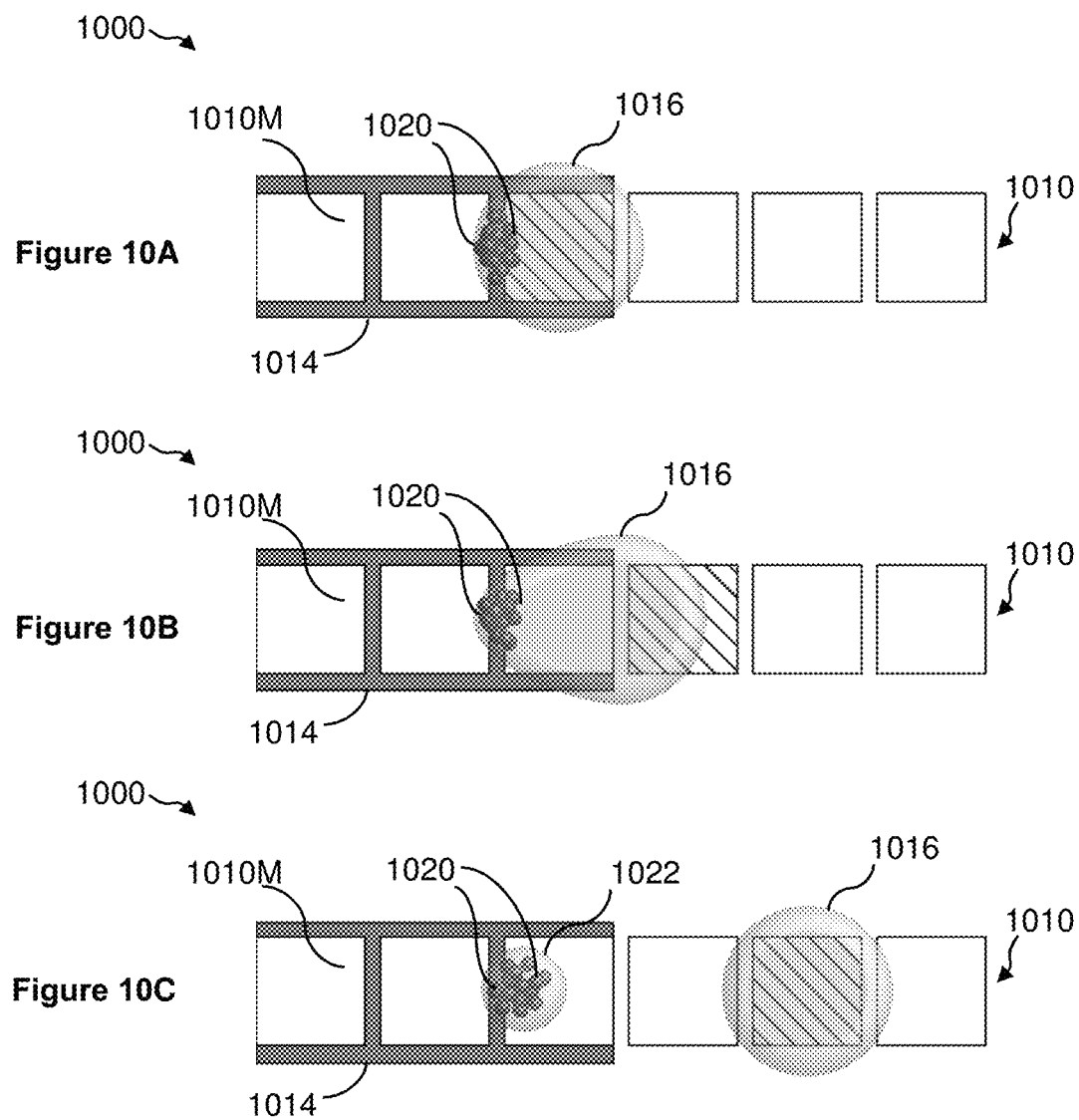

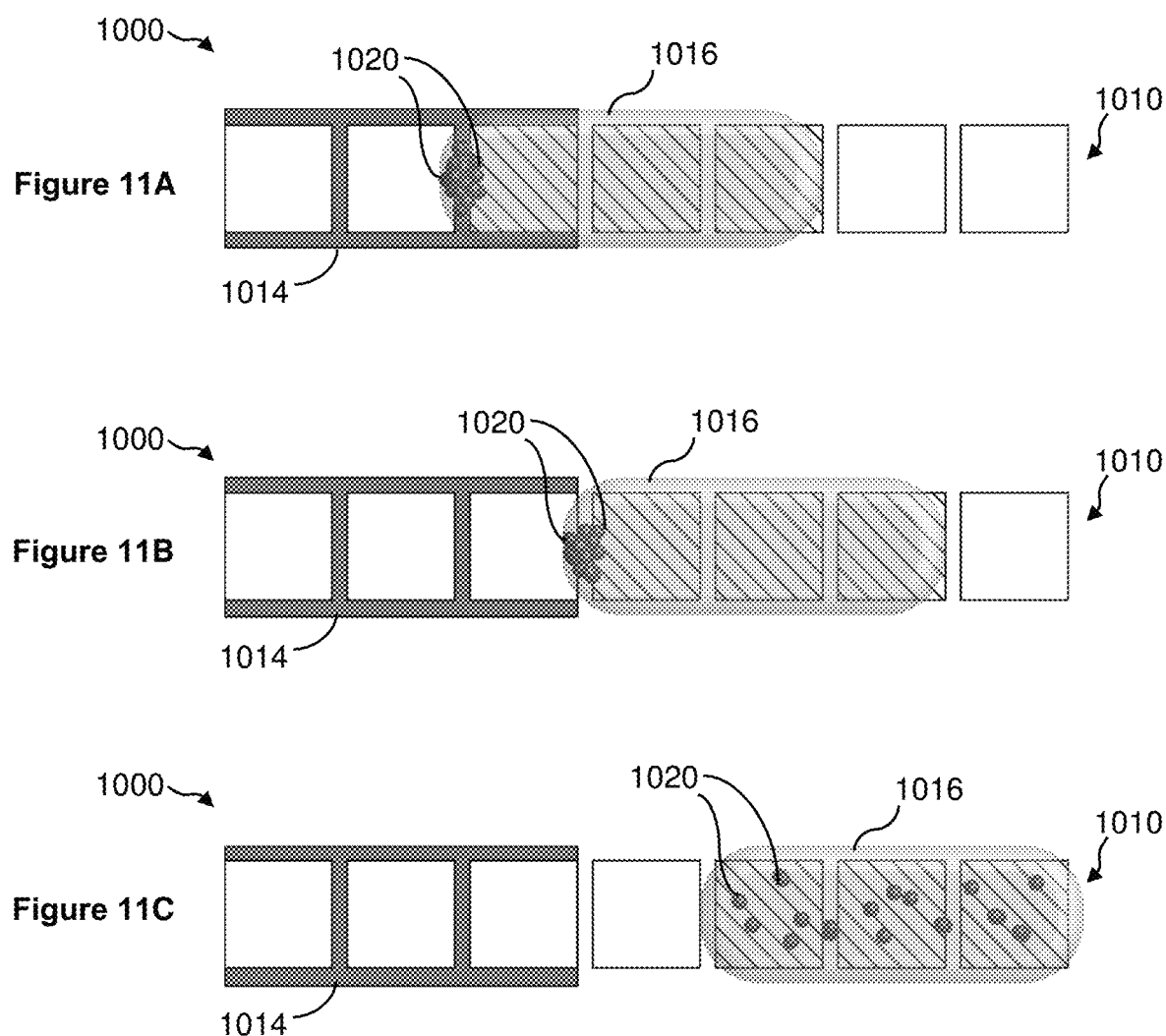

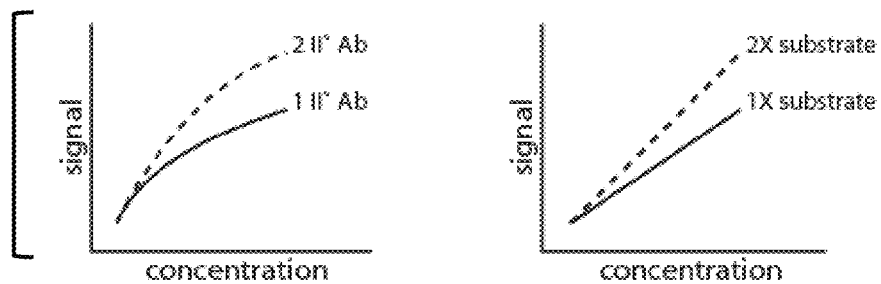

1400

BEAD INCUBATION AND WASHING ON A DROPLET ACTUATOR

RELATED APPLICATIONS

This application is a divisional of and incorporates by reference U.S. patent application Ser. No. 15/210,634, entitled "Bead Incubation and Washing on a Droplet Actuator" filed Jul. 14, 2016, which is a continuation of and incorporates by reference U.S. patent application Ser. No. 14/731,740 (now U.S. Pat. No. 9,395,361 issued Jul. 19, 2016), entitled "Bead Incubation and Washing on a Droplet Actuator" filed on Jun. 5, 2015, which is a continuation of and incorporates by reference U.S. patent application Ser. No. 14/466,193 (now U.S. Pat. No. 9,081,007 issued Jul. 14, 2015), entitled "Bead Incubation and Washing on a Droplet Actuator" filed on Aug. 22, 2014, which is a continuation of and incorporates by reference U.S. patent application Ser. No. 14/081,376 (now U.S. Pat. No. 8,846,410 issued Sep. 30, 2014), entitled "Bead Incubation and Washing on a Droplet Actuator" filed on Nov. 15, 2013, which is a divisional of and incorporates by reference U.S. patent application Ser. No. 13/081,927 (now U.S. Pat. No. 8,637,324 issued Jan. 28, 2014), entitled "Bead Incubation and Washing on a Droplet Actuator" filed on Apr. 7, 2011, which is a continuation-in-part of U.S. patent application Ser. No. 11/639,531 (now U.S. Pat. No. 8,613,889 issued Dec. 24, 2013), entitled "Droplet-based washing" filed on Dec. 15, 2006. U.S. patent application Ser. No. 14/466,193 (now U.S. Pat. No. 9,081,007 issued Jul. 14, 2015), is a continuation-in-part of U.S. patent application Ser. No. 11/639,736 (now U.S. Pat. No. 7,439,014 issued Oct. 21, 2008), entitled "Droplet-Based Surface Modification and Washing" filed on Dec. 15, 2006; Ser. No. 12/113,385 (now U.S. Pat. No. 8,541,176 issued Sep. 24, 2013), entitled "Droplet-Based Surface Modification and Washing" filed on May 1, 2008, the application of which is a divisional of and incorporates by reference U.S. patent application Ser. No. 11/639,736 (now U.S. Pat. No. 7,439,014 issued Oct. 21, 2008); Ser. No. 12/615,609 (now U.S. Pat. No. 8,313,895 issued Nov. 20, 2012), entitled "Droplet-Based Surface Modification and Washing" filed on Oct. 10, 2009, the application of which is a continuation of and incorporates by reference U.S. patent application Ser. No. 12/113,385 (now U.S. Pat. No. 8,541,176 issued Sep. 24, 2013), which is a divisional of U.S. patent application Ser. No. 11/639,736 (now U.S. Pat. No. 7,439,014 issued Oct. 21, 2008); and Ser. No. 12/615,666, entitled "Droplet-Based Surface Modification and Washing" filed on Nov. 10, 2009, the application of which is a continuation of and incorporates by reference U.S. patent application Ser. No. 12/113,385 (now U.S. Pat. No. 8,541,176 issued Sep. 24, 2013), which is a divisional of U.S. patent application Ser. No. 11/639,736 (now U.S. Pat. No. 7,439,014 issued Oct. 21, 2008). U.S. patent application Ser. No. 11/639,531 (now U.S. Pat. No. 8,613,889 issued Dec. 24, 2013) and Ser. No. 11/639,736 (now U.S. Pat. No. 7,439,014 issued Oct. 21, 2008) claim priority to and incorporate by reference related provisional U.S. Provisional Patent Application Nos. 60/745,058, entitled "Filler Fluids for Droplet-Based Microfluidics" filed on Apr. 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and Method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; and 60/807,104, entitled "Method and Apparatus for DropletBased Nucleic Acid Amplification," filed on Jul. 12, 2006.

Additionally, U.S. patent application Ser. No. 13/081,927 (now U.S. Pat. No. 8,637,324 issued Jan. 28, 2014), is a continuation of, claims priority to, and incorporates by reference International Patent Application Ser. No. PCT/US2009/059868, entitled "Bead Incubation And Washing On A Droplet Actuator" International filing date of Oct. 7, 2009, the application of which claims priority to U.S. Provisional Patent Application Nos. 61/103,302, filed on Oct. 7, 2008, entitled "Bead Incubation and Washing on a Droplet Actuator" and 61/122,791, filed on Dec. 16, 2008, entitled "Bead Incubation and Washing on a Droplet Actuator," the entire disclosures of which are incorporated herein by reference.

GRANT INFORMATION

This invention was made with government support under AI066590, HG003706, and CA114993 awarded by the National Institutes of Health. The United States Government has certain rights in the invention.

Each of the patents and patent applications provided herein is incorporated by reference in its entirety.

FIELD OF THE INVENTION

The present invention provides methods and apparatuses for incubating and washing magnetically responsive beads on a droplet actuator. More specifically the present invention provides methods for incubating magnetically responsive beads that are labeled with primary antibody, a sample (i.e., analyte), and secondary reporter antibodies on a magnet, on and off a magnet, and completely off a magnet. The invention also provides methods for washing magnetically responsive beads using shape-assisted merging of droplets. The invention also provides methods for shape-mediated splitting, transporting, and dispensing of a sample droplet that contains magnetically responsive beads. The methods of the invention provide for rapid time to result and optimum detection of an analyte in an immunoassay.

BACKGROUND OF THE INVENTION

Droplet actuators are used to conduct a wide variety of droplet operations. A droplet actuator typically includes two substrates separated by a gap. The substrates include electrodes for conducting droplet operations. The gap between the substrates is typically filled with a filler fluid that is immiscible with the fluid that is to be subjected to droplet operations. Droplet operations are controlled by electrodes associated with one or both of the substrates. Droplet actuators are used in a variety of applications, including molecular diagnostic assays, such as immunoassays where time to result is directly affected by the protocols used for each step of the assay. The most time consuming steps in an immunoassay are incubation and washing. "Time to result" is directly affected by the protocols used for incubation, the duration of time for incubating the antibodies and the antigens, and the duration of time for incubating the substrate with sandwich beads, all of which may depend on the mixing efficiency within the droplets and the reaction and binding kinetics. The amount of washing required to obtain the required sensitivity may also influence the total time to result for immunoassays. There is a need for efficient incubation and washing protocols for immunoassays on a droplet actuator that provide for rapid time to result and optimum detection of an analyte.

BRIEF DESCRIPTION OF THE INVENTION

The present invention is directed to bead incubation and washing on a droplet actuator. The methods described herein may include providing a droplet including one or more magnetically responsive beads. The methods may include exposing the magnetically responsive beads in the droplet to a first region of a magnetic field capable of substantially attracting magnetically responsive beads in the droplet. The methods may include separating the droplet from the first region of the magnetic field, the magnetically responsive beads remaining in the magnetic field. The magnetically responsive beads may be separated from the droplet while exposing the magnetically responsive beads in the droplet to a first region of a magnetic field and/or while the droplet is being separated from the first region of the magnetic field. Exposing the magnetically responsive beads in the droplet to a first region of a magnetic field may include transporting the droplet into the first region of the magnetic field and/or transporting the first region of the magnetic field into proximity with the magnetically responsive beads. Separating the droplet from the first region of the magnetic field may include transporting the droplet away from the first region of the magnetic field and/or moving the first region of the magnetic field away from the droplet.

In one embodiment, a method of incubating droplets having magnetically responsive beads is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method also comprises positioning a droplet having magnetically responsive beads therein at a location on the droplet operations surface within the first region of the magnetic field to form a concentration of beads in the droplet; transporting the droplet through activation of selected droplet operations electrodes away from the first region of the magnetic field, thereby resuspending the magnetically responsive beads in the droplet; operating the droplet operations electrodes to cause the droplet to split into two droplets, thereby redistributing the magnetically responsive beads; and operating the droplet operations electrodes to merge the two droplets into a single droplet.

In another embodiment, a method of incubating droplets having magnetically responsive beads therein is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method also comprises positioning a droplet having magnetically responsive beads therein at a location within the first region of the magnetic field of the magnet to form a concentration of beads in the droplet; transporting the droplet through activation of selected droplet operations electrodes away from the first region of the magnetic field of the magnet to resuspend the magnetically responsive beads in the droplet; operating the droplet operations electrodes to cause the droplet to elongate and then split into two droplets at a location away from the magnet; and operating the droplet operations electrodes to merge the two droplets into a single droplet at a location away from the magnet, whereby the transporting, splitting, and merging comprise an incubation cycle.

In yet another embodiment, a method of incubating droplets having magnetically responsive beads therein is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method further comprises positioning a droplet having magnetically responsive beads therein on a droplet operations electrode, the droplet having a footprint approximately two times the area of a single droplet operations electrode; transporting the droplet through activation of selected droplet operations electrodes in one direction in a manner elongating the droplet; and operating the droplet operations electrodes in a manner to cause the droplet to be transported in an opposite direction to cause mixing and incubation within the droplet.

In a further embodiment, a method of washing magnetically responsive beads for separating and removing unbound material is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method further comprises positioning a droplet having magnetically responsive beads therein to have a first region of the droplet within the first region of the magnetic field to form a concentration of beads; at another end of the magnetic field, positioning a wash buffer droplet such that a first region of the wash buffer droplet is within the first region of the magnetic field; operating the droplet operations electrodes to merge the droplet and the wash droplet to cause redistribution of beads; operating the droplet operation electrodes to cause the merged droplet to partially move away from the magnet, and to cause beads in the droplet to concentrate in the merged droplet; and operating the droplet operations electrodes to split the merged droplet to form a supernatant droplet containing unbound reagents.

In a still further embodiment, a method of resuspending magnetically responsive beads between wash cycles is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method further comprises positioning a droplet having magnetically responsive beads therein at a location partially overlapping the first region of the magnetic field; transporting the droplet through activation of selected droplet operations electrodes away from the first region of the magnetic field; operating the droplet operations electrodes to cause the droplet to move towards the first region of the magnetic field; and repeating the transporting and operating steps to cause sufficient resuspension of beads such that unbound material may be effectively removed in subsequent wash cycles.

In another embodiment, a droplet actuator device having a structure for conducting a bead washing protocol is provided and comprises an array of droplet operations electrodes configured to provide a plurality of individual wash lanes, and a single waste lane intersecting each one of the plurality of wash lanes; and waste wells associated at the end of each one of the plurality of wash lanes, and at the end of the single waste lane.

In yet another embodiment, a method of separating magnetically responsive beads from a droplet is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method further comprises positioning a droplet having magnetically responsive beads therein within the first region of the magnetic field of the magnet to cause the magnetically responsive beads to be attracted to the magnet, and activating the droplet operations surface to cause the droplet to be circular in shape; operating the droplet operations surface to cause the droplet to move away from the first region of the magnetic field to form a concentration of magnetically responsive beads in the droplet, and the droplet operations surface being operated to cause the droplet to be transported away from the magnet one droplet operations electrode at a time, to cause the geometry of the droplet to be distorted; and continuing to transport the droplet away from the magnet to cause the concentration of magnetically responsive beads to break away from the droplet to result in a relatively small and highly concentrated magnetically responsive bead droplet left behind and held immobilized by the magnet.

In a further embodiment, a method of transporting magnetically responsive beads within droplets is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method further comprises positioning a droplet having magnetically responsive beads located therein at a location wherein the droplet partially overlaps the magnet; operating the droplet operations electrodes to subject an edge of the droplet nearest the magnet to both a magnetic force from the first region of the magnetic field and an electrowetting force from the droplet operations electrodes, and to subject an edge of the droplet furthest from the magnet only to an electrowetting force, to cause the droplet to be transported away from the magnet while retaining the magnetically responsive beads within the droplet; and continuing to transport the droplet away from the magnet to cause the magnetically responsive beads to be redistributed within the droplet.

In a still further embodiment, a method of separating beads from a droplet onto a magnet is provided and comprises providing a droplet actuator comprising droplet operations electrodes arranged for conducting droplet operations on a droplet operations surface and a magnet positioned relative to the droplet operations surface such that a droplet controlled by one or more of the droplet operations electrodes may be positioned within or away from a first region of the magnet's magnetic field capable of substantially attracting magnetically responsive beads in the droplet. The method further comprises positioning a droplet having magnetically responsive beads therein within the first region of the magnetic field of the magnet to cause the beads to be attracted to the magnet, and activating the droplet operations surface in a manner to cause the droplet to take an elongate shape; operating the droplet operations surface to activate one electrode at a time, to cause the droplet to move away from the magnet, and thereby cause the geometry of the droplet to be distorted; and continuing to operate the droplet operations surface to transport the droplet further away from the magnet and inactivating an electrode intermediate to the droplet to cause the droplet to split into a supernatant droplet and a smaller droplet that has the magnetically responsive beads therein.

In another embodiment, a droplet actuator structure for extracting DNA from a sample is provided and comprises at least six on-actuator reservoirs interconnected for storing and dispensing different reagents onto the droplet actuator; and the reservoirs interconnected through paths of droplet operations electrodes, including at least two paths having magnets associated therewith, and a bead collection reservoir connected to the six on-actuator reservoirs through the droplet operations electrodes paths.

In yet another embodiment, a method of extracting DNA from whole blood is provided and comprises using a droplet actuator comprising at least six on-actuator reservoirs interconnected for storing and dispensing different reagents onto the droplet actuator; and the reservoirs interconnected through paths of droplet operations electrodes, including at least two paths having magnets associated therewith, and a bead collection reservoir connected to the six on-actuator reservoirs through the droplet operations electrodes paths. The method further comprises dispensing a droplet of magnetically responsive beads suspended in a lysis buffer from a first of the six on-actuator reservoirs, and transporting the droplet through the droplet operations electrodes to a specific location having one of the magnets associated with the location, to hold the magnetically responsive beads within the droplet thereon; dispensing droplets of whole blood from a second reservoir and lysis buffer from a third reservoir into a fourth mixing reservoir to be mixed therein to form a cell lysate; dispensing droplets of the cell lysate across the magnetically responsive beads in succession and removing supernatant from the droplets while holding the magnetically responsive beads; dispensing wash droplets from at least a fifth reservoir to wash the magnetically responsive beads to remove cell debris; and eluting and collecting DNA captured on the magnetically responsive beads at the bead collection reservoir.

In a further embodiment, a method of detecting a component in a sample is provided and comprises providing a droplet actuator comprising droplet operations electrodes arranged for conducting droplet operations on a droplet operations surface; a magnet positioned related to the droplet operations surface such that a droplet controlled by one of more droplet operations electrodes may be positioned within or away from a first region of the magnet's magnetic field capable of substantially attracting magnetically responsive beads in the droplet; and a wash reservoir at one end of the arrangement of droplet operations electrodes. The method further comprises positioning a droplet having magnetically responsive beads located therein, the magnetically responsive beads being coated with an antibody having an affinity for a specific target antigen, away from the magnet; operating the droplet operations surface in a manner to repeatedly transport the droplet back and forth, away from the magnet, in a manner to provide sufficient resuspension and mixing of the magnetically responsive beads for antibody and antigen binding; operating the droplet operations surface in a manner to transport the droplet to a location within the first region of the magnetic field, and splitting off a supernatant droplet from the droplet by selectively operating the droplet operations surface, and retaining the magnetically responsive beads at the magnet; operating the droplet operations electrodes to transport a reagent droplet to the droplet operations electrode in the first region of the magnetic field to merge the reagent droplet with the droplet containing the magnetically responsive beads, and transporting the merged droplet back and forth, at a location away from the magnet, to cause incubation; and transporting the merged droplet through operation of the droplet operations electrodes to the droplet operations electrode at the magnet and splitting off a supernatant droplet through operation of the droplet operations electrodes.

DEFINITIONS

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator.

Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet Actuator" means a device for manipulating droplets. For examples of droplets, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006, the disclosures of which are incorporated herein by reference. Methods of the invention may be executed using droplet actuator systems, e.g., as described in International Patent Application No. PCT/US2007/009379, entitled "Droplet manipulation systems," filed on May 9, 2007. In various embodiments, the manipulation of droplets by a droplet actuator may be electrode mediated, e.g., electrowetting mediated or dielectrophoresis mediated.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; condensing a droplet from a vapor; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. In various embodiments, the droplet operations may be electrode mediated, e.g., electrowetting mediated or dielectrophoresis mediated.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; and in International Patent Application No. PCT/US2008/072604, entitled "Use of additives for enhancing droplet actuation," filed on Aug. 8, 2008.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure.

The terms "top" and "bottom" are used throughout the description with reference to the top and bottom substrates of the droplet actuator for convenience only, since the droplet actuator is functional regardless of its position in space.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is capable of substantially attracting any magnetically responsive beads in the droplet.

When a liquid in any form (e.g., a droplet or a continuous body, whether movingor stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

BRIEF DESCRIPTION OF THE DRAWINGS

FIGS. 7A, 7B, 7C, and 7D illustrate top views of an example of a region of a droplet actuator of FIGS. 5A through 5E and show a process of resuspending magnetically responsive beads between wash cycles;

FIGS. 10A, 10B, and 10C show a top view of a region of a droplet actuator and a process of separating beads from a sample droplet;

FIGS. 11A, 11B, and 11C show a top view of a region of a droplet actuator of FIGS. 10A through 10C and a process of transporting beads within a droplet;

FIGS. 13A and 13B show a comparison of bench top and droplet actuator immunoassay reagent ratios and a plot of reagent concentration versus signal strength, respectively, that provide for optimum droplet based immunoassay performance;

DETAILED DESCRIPTION OF THE INVENTION

Figure 1:
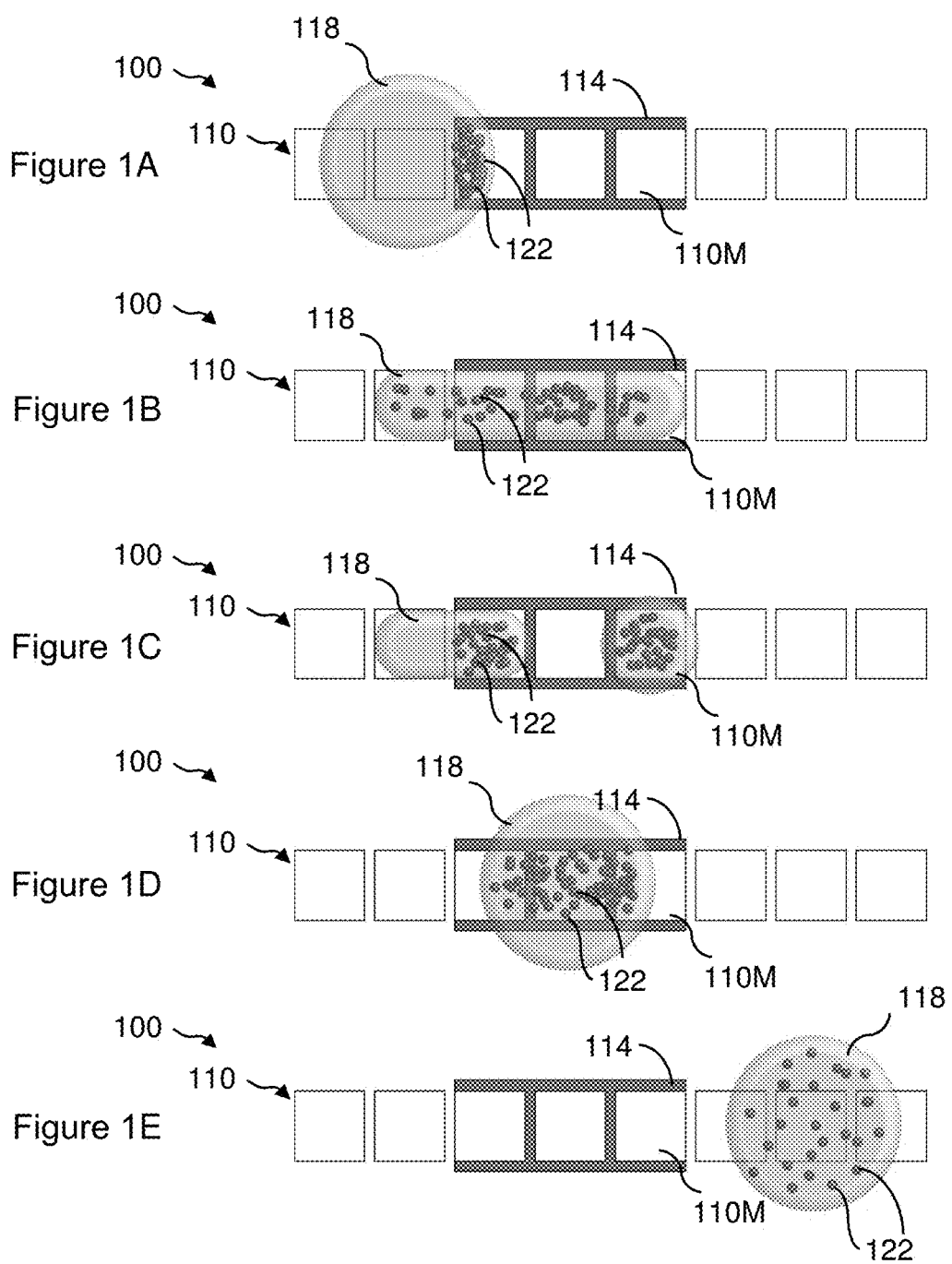
FIGS. 1A, 1B, 1C, 1D, and 1E illustrate top views of an example of a region of a droplet actuator and show a process of incubating beads on a magnet.
Figure 2:
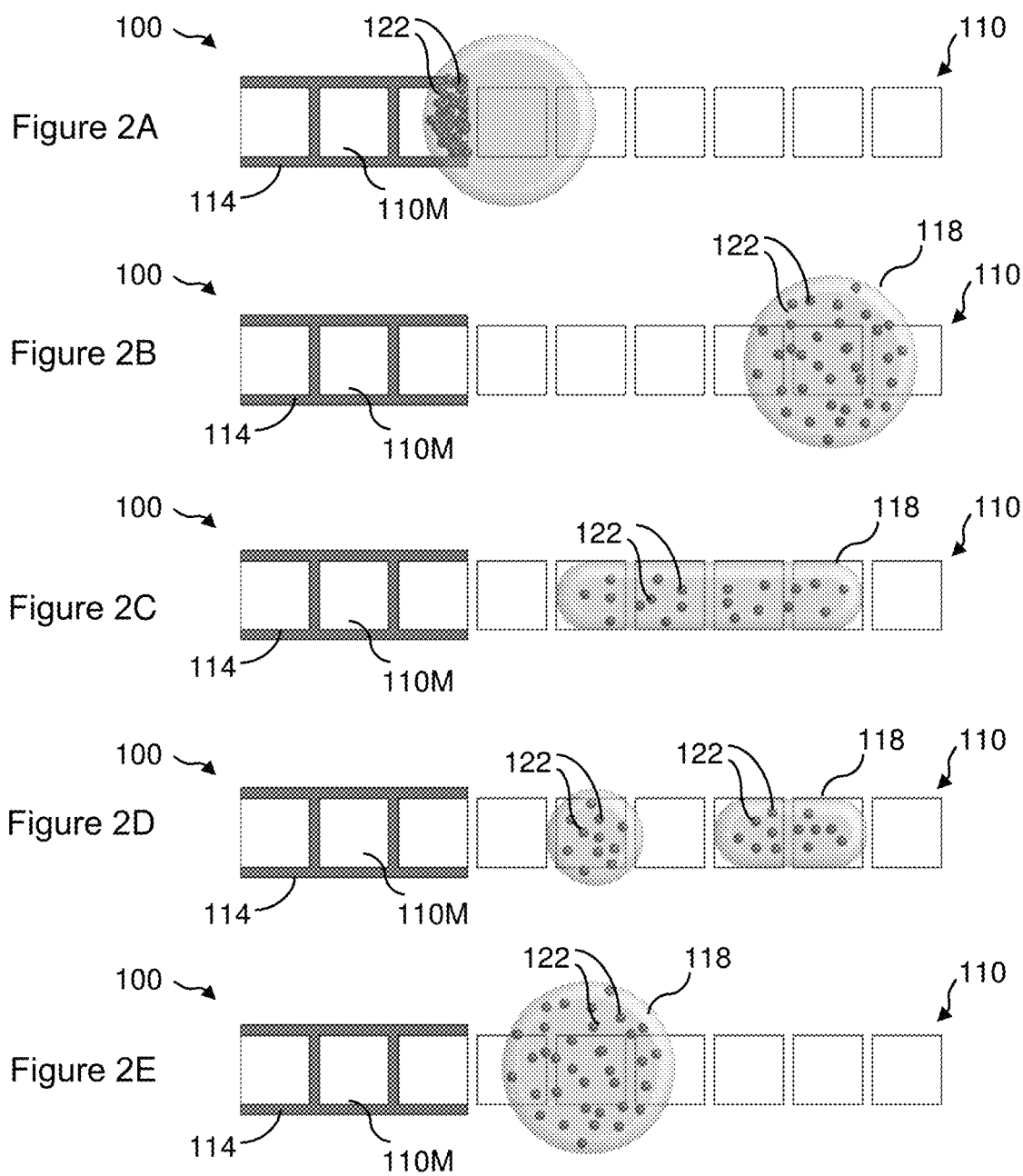
FIGS. 2A, 2B, 2C, 2D, and 2E illustrate top views of an example of a region of a droplet actuator of FIGS. 1A through 1E and show a process of incubating droplets that include magnetically responsive beads on and off a magnet.

The present invention provides methods and apparatuses for incubating and washing magnetically responsive beads on a droplet actuator. More specifically the present invention provides methods for incubating magnetically responsive beads that are labeled with primary antibody, a sample (i.e., analyte), and secondary reporter antibodies on a magnet, on and off a magnet, and completely off a magnet. The invention also provides methods for washing magnetically responsive beads using shape-assisted merging of droplets. The invention also provides methods for shape-mediated splitting, transporting, and dispensing of a sample droplet that contains magnetically responsive beads. The methods of the invention provide for rapid time to result and optimum detection of an analyte in an immunoassay.

In an alternative embodiment of the invention, a droplet actuator may be used to extract human genomic DNA from a sample.

Incubation Protocols

Incubation protocols on a droplet actuator are generally comprised of transporting a droplet (e.g., a droplet that includes an antigen, primary capture antibodies conjugated to magnetically responsive beads, and secondary reporter antibodies) along a path of electrodes by use of splitting and merging operations that are inserted between transport cycles. Transporting, splitting, and merging the droplet ensures that the beads are well distributed (i.e., mixed) within the droplet. An incubation cycle (e.g., transport, split, and merge) may be repeated two or more times. The high mixing efficiency provided by a series of incubation cycles provides for sufficient antigen-antibody binding.

Magnetically responsive beads have a tendency to settle and form aggregates due to gravity and/or continued exposure to strong magnetic forces. These aggregates reduce the available surface area for binding and slow down reaction kinetics and, consequently, the time to result and sensitivity of the assay. Moreover, interstices in magnetically responsive bead aggregates can hold unbound species that leads to ineffective washing. This may result in less sensitive assays and inaccuracies between assays due to differing amounts of unbound species held in the interstices. Therefore, it is useful to keep the beads dispersed or resuspended during incubation and in the steps immediately following separation for further processing of the droplets away from the magnets. Resuspension of magnetically responsive beads within droplets, akin to rigorous vortexing of bench scale systems, may be achieved by moving the bead droplet back and forth and exploiting the inherent circulatory flow patterns that are developed during droplet transport.

FIGS. 1A, 1B, 1C, 1D, and 1E illustrate top views of an example of a region of a droplet actuator 100 and show a process of incubating droplets that include magnetically responsive beads on a magnet. The method of the invention of FIGS. 1A through 1E is an example of an incubation method wherein a droplet is transported into the magnetic field of a magnet and a series of split and merge droplet operations are performed to resuspend the beads within the droplet. Because of the magnet field, resuspension of the beads is primarily in the X-Y direction.

Droplet actuator 100 may include a path or array of droplet operations electrodes 110 (e.g., electrowetting electrodes). A magnet 114 is arranged in close proximity to droplet operations electrodes 110. In particular, magnet 114 is arranged such that certain droplet operations electrodes 100 (e.g., 3 droplet operations electrodes 110M) are within the magnetic field of magnet 114. Magnet 114 may, for example, be a permanent magnet or an electromagnet. Droplet actuator 100 may contain a droplet 118 that may be transported along droplet operations electrodes 110 via electrowetting and upon which droplet operations may be performed. Droplet 118 may, for example, be a 3× droplet, meaning that its footprint is approximately 3 times the area of one droplet operations electrode 110. Droplet 118 may, for example, include 1 part magnetically responsive beads and 2 parts sample. Droplet 118 may, for example, be a sample droplet that includes an analyte (e.g., an antigen) to be evaluated.

Droplet 118 may include one or more beads 122, which may be magnetically responsive beads. Beads 122 may have an affinity for certain target substances, such as, for example, a certain type of cell, protein, nucleic acid and/or antigen. In one example, beads 122 are coated with a primary antibody with affinity for a specific target antigen.

FIG. 1A shows a first step in a process of incubating droplets that includes magnetically responsive beads on a magnet. In this step, droplet 118 that has beads 122 therein is positioned adjacent to and overlapping droplet operations electrodes 110M, which is within the magnetic field of magnet 114. Because beads 122 are magnetically responsive, a concentration of beads is formed at the side of droplet 118 that is closest to magnet 114.

FIG. 1B shows another step in the process of incubating droplets that include magnetically responsive beads on a magnet. In this step, droplet 118 is transported via electrowetting to adjacent electrodes 110M and takes on a slug-shaped geometry. Typically, two droplet operations electrodes 110 may be used to transport a 3× droplet 118. Because beads 122 are magnetically responsive, a concentration of beads 122 is formed at the bottom of droplet 118 (e.g., on the surface of droplet actuator 100) and at the center of magnet 114. Elongation of droplet 118 to a slug geometry provides for sufficient flow of fluid within droplet 118 to resuspend beads 122 in droplet 118.

FIG. 1C shows yet another step in the process of incubating droplets that include magnetically responsive beads on a magnet. In this step, droplet 118 is split near the central region of magnet 114 using droplet operations to form, for example, two sample droplets. Splitting of droplet 118 provides for redistribution of beads 122 within the sample droplets.

FIG. 1D shows yet another step in the process of incubating droplets that include magnetically responsive beads on a magnet. In this step, split droplet 118 is merged on magnet 114 using droplet operations to form a single droplet 118. The transporting, splitting, and merging operations of FIGS. 1B, 1C, and 1D comprise an incubation cycle. Several incubation cycles may be performed to provide for resuspension and redistribution (i.e., mixing) of beads 122 in droplet 118.

FIG. 1E shows yet another step in the process of incubating droplets that include magnetically responsive beads on a magnet. In this step, magnet 114, which is, for example, an electromagnet, is not activated. Therefore, no magnetic field is generated by magnet 114 and beads 122 of droplet 118 have no attraction to magnet 114. Droplet 118 is transported via electrowetting to adjacent electrodes 110. Beads 122 are resuspended in droplet 118.

FIGS. 2A, 2B, 2C, 2D, and 2E illustrate top views of an example of a region of a droplet actuator 100 of FIGS. 1A through 1E and show a process of incubating, on and off a magnet, droplets that include magnetically responsive beads. The method of the invention of FIGS. 2A through 2E is an example of an incubation method wherein a droplet is transported near the magnetic field of a magnet and then away from the magnet to perform a series of split and merge droplet operations that are used to resuspend the beads within the droplet. Because the split and merge operations are performed away from the magnet, resuspension of the beads is in the lateral X-Y, and vertical Z directions.

The steps shown in FIGS. 2A, 2B, 2C, 2D, and 2E are substantially the same as those that are described in FIGS. 1A, 1B, 1C, 1D, and 1E except that, instead of incubating droplet 118 on droplet operations electrodes 110M, droplet incubation is performed adjacent to magnet 114 and away from magnet 114 on droplet operations electrodes 110.

FIG. 2A shows a first step in a process of incubating droplets that include magnetically responsive beads on and off a magnet. In this step, droplet 118 that has beads 122 therein is positioned adjacent to droplet operations electrodes 110M, which is within the magnetic field of magnet 114. Because beads 122 are magnetically responsive, a concentration of beads is formed at the side of droplet 118 that is closest to magnet 114.

FIG. 2B shows another step in a process of incubating, on and off a magnet, droplets that include magnetically responsive beads. In this step, droplet 118 is transported via electrowetting away from the magnetic field of magnet 114. Beads 122 are sufficiently resuspended in droplet 118.

FIG. 2C, 2D, and 2E show the process steps of droplet elongation (i.e., formation of slug-shaped geometry), droplet splitting and droplet merging, respectively, that are used to provide for sufficient flow of fluid within droplet 118 to resuspend and redistribute beads 122 in droplet 118. Because the split and merge operations are performed away from the magnet, resuspension of the beads is in the X, Y, and Z directions.

FIGS. 3A, 3B, 3C, 3D, and 3E illustrate top views of an example of a region of a droplet actuator 300 and show a process of incubating droplets that include magnetically responsive beads substantially out of the magnetic field of a magnet. The method of the invention of FIGS. 3A through 3E is an example of an incubation method wherein a series of droplet transport operations are used to resuspend the beads within the droplet. Because the droplet operations are performed a sufficient distance away from a magnet, resuspension of the beads is in the lateral X-Y, and vertical Z directions.

Droplet actuator 300 is substantially the same as droplet actuator 100 of FIGS. 1A through 1E except that it is configured to support droplet operations on a 2× droplet. In this embodiment, droplet 118 is a 2× droplet, meaning that its footprint is approximately 2 times the area of one droplet operations electrode. Droplet 118 may, for example, include 1 part magnetically responsive beads and 1 part sample. Alternatively, droplet 118 may include 1 part sample plus magnetically responsive beads and 1 part secondary reporter antibody.

FIGS. 3A through 3E show the process steps of transporting droplet 118 along a linear path of droplet operation electrodes 110 to provide mixing of magnetically responsive beads 122. The use of a 2× droplet provides several advantages over the use of a 3× droplet in a droplet actuator-based immunoassay. For example, mixing a 2× droplet using two droplet operations electrodes is more efficient than mixing a 3× droplet using two droplet operations electrodes. The concentration of magnetically responsive beads is also higher in a 2× droplet than a 3× droplet. A higher concentration of magnetically responsive beads provides for increased binding rate. Because the incubation cycle of a 2× droplet is substantially out of the magnetic field of magnet 114, the binding efficiency is also increased. In addition, transport of a 3× droplet in proximity to a magnetic field via electrowetting using 2 droplet operation electrodes may result in the formation of a tail in which magnetically responsive beads may aggregate. The formation of bead aggregates may result in reduced binding efficiency.

Figure 4:
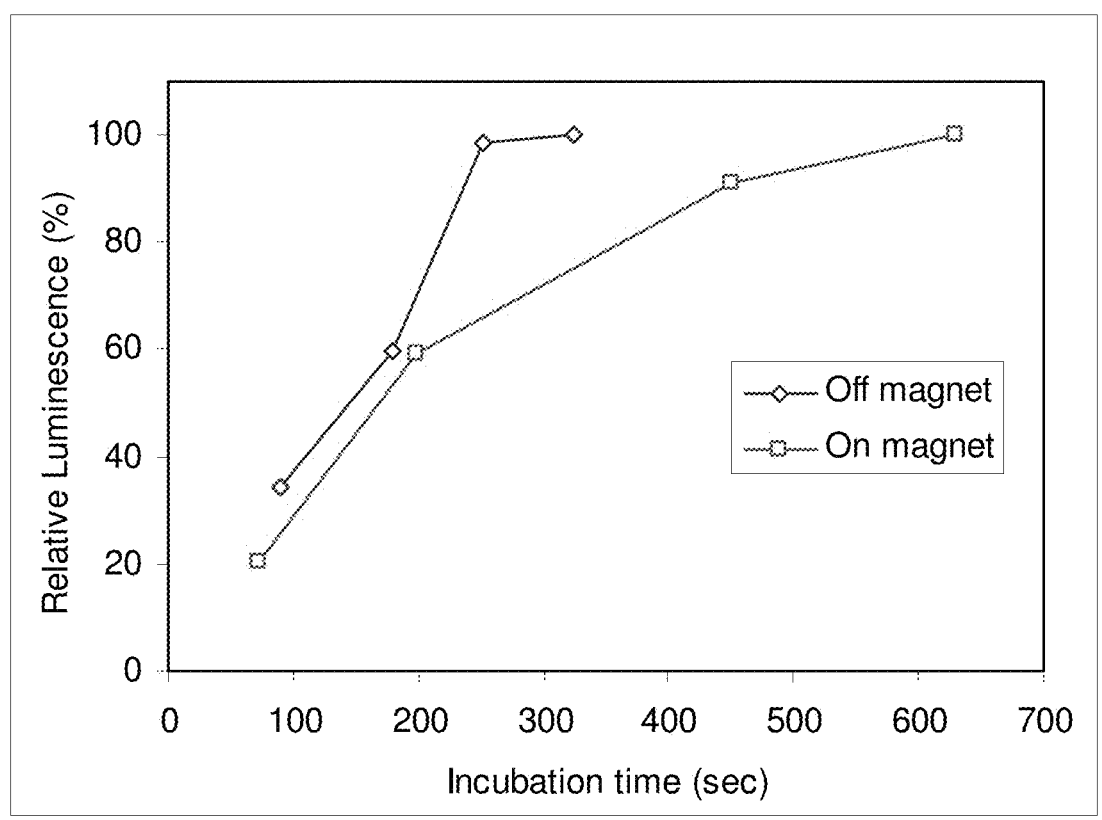
FIG. 4 shows a plot of a comparison of incubation time between on-magnet and off-magnet incubation protocols of FIG. 1 and FIG. 2, respectively, on immunoassay performance measured in chemiluminescence.

FIG. 4 shows a plot 400 of a comparison of incubation time between on-magnet and off-magnet incubation protocols on immunoassay performance measured in chemiluminescence. Data was generated using the incubation protocols of FIG. 1 (on-magnet) and FIG. 2 (off-magnet). Immunoassays were performed on a 300 nanoliter (nL) droplet that contained capture antibody magnetically responsive beads, alkaline phosphatase (ALP)-labeled reporter antibodies and 5 ng/mL Troponin I (TnI). Four immunoassays were performed on the magnet with incubation times of 72 seconds (sec), 198 sec, 450 sec, and 630 sec. Four more immunoassays were performed off the magnet with incubation times of 90 sec, 180 sec, 252 sec, and 324 sec. Droplet operations were the same for each incubation protocol.

As shown in FIG. 4, when incubation was performed on the magnet, the time to reach saturation was almost doubled the time to reach saturation when compared to incubation performed off the magnet. The difference in time to reach saturation between the two protocols may occur because in the presence of a magnet, the magnetically responsive beads are attracted to the surface of the droplet actuator and the recirculation patterns produce within a droplet would resuspend the magnetically responsive beads only in the lateral plane (X-Y) direction. When incubation is performed off the magnet and a sufficient distance away from the magnet (e.g., more than 2 droplet operations electrodes), resuspension of the magnetically responsive beads is in both the lateral plane (X-Y direction) and vertical plane (Z direction). Resuspension of the beads in the X, Y, and Z directions provides more surface area for binding reactions and increased rate of reaction.

In another embodiment, an incubation protocol may include merging of a circular bead droplet on a magnet with two circular sample droplets. Mixing in the merged droplet is provided by moving the merged droplet back and forth on droplet operations electrodes while the magnetically responsive beads are immobilized on the magnet.

In yet another embodiment, an incubation protocol may include merging of a circular bead droplet on a magnet with a 4×, 5× elongated (slug-shaped) sample droplet. Mixing in the merged slug-shaped droplet is provided by moving the merged droplet back and forth on droplet operations electrodes while the magnetically responsive beads are immobilized on the magnet.

Washing Protocols

Washing of magnetically responsive beads, where unbound molecules are separated and removed, is one of the most critical steps in implementing an immunoassay in a digital microfluidic system. In some embodiments, washing is performed using a merge-and-split protocol, which is repeated until the unbound material is sufficiently depleted from the supernatant to permit accurate and precise detection.

FIGS. 5A, 5B, 5C, 5D, and 5E show a top view of a region of a droplet actuator 500 and a process of washing magnetically responsive beads using shape-assisted merging of droplets. The method of the invention of FIGS. 5A through 5E is an example of a wash method wherein a wash buffer droplet and a magnetically responsive bead droplet are elongated in a slug-shaped geometry and series of merge and split operations are used to remove unbound material from a bead droplet. The merge and split operations provide for substantially complete fluid replacement of unbound supernatant with wash buffer in the absence of mixing.

Droplet actuator 500 may include a path or array of droplet operations electrodes 510 (e.g., electrowetting electrodes). A magnet 512 is arranged in close proximity to droplet operations electrodes 510. In particular, magnet 512 is arranged such that certain droplet operations electrodes 510 (e.g., 3 droplet operations electrodes 510M) are within the magnetic field of magnet 512. Magnet 512 may, for example, be a permanent magnet or an electromagnet. Droplet actuator 500 may contain a wash buffer droplet 516 and a bead droplet 514 that may be transported along droplet operations electrodes 510 via electrowetting and upon which droplet operations may be performed. Bead droplet 514 may, for example, include a quantity of magnetically responsive beads 518 that includes bound antigen and reporter antibody (i.e., antigen-antibody-reporter complex), and unbound material such as excess unbound reporter antibody.

Bead droplet 514 and wash buffer droplet 516 may, for example, be 2× droplets, meaning that their footprint is approximately 2 times the area of one dropletoperations electrode 510. Bead droplet 514 and wash buffer droplet 516 may be configured as slug-shaped droplets (i.e., elongated droplets) by performing droplet operations on the 2× droplets using two active droplet operations electrodes 510. Because the excess droplet volume is now spread over a second active droplet operations electrode 510, the droplets are elongated and conform to the shape of two electrodes.

FIG. 5A shows a first step in a process of washing beads using shape-assisted merging of droplets. In this step, bead droplet 514 that has beads 518 therein is positioned such that one region of droplet 514 is on a droplet operations electrodes 510M which is within the magnetic field of magnet 512 and a second region of droplet 514 is on an adjacent droplet operations electrode 510. Because beads 518 are magnetically responsive, a concentration of beads is formed at the side of bead droplet 514 that is closest to magnet 512. At the opposite end of magnet 512, wash buffer droplet 516 is similarly positioned such that one region of wash buffer droplet 516 is on a droplet operations electrodes 510M which is within the magnetic field of magnet 512 and a second region of droplet 516 is on an adjacent droplet operations electrode 510. The timing of the sequence of droplet operations for merging bead droplet 514 and wash buffer 516 is such that bead droplet 514 is elongated to a slug-shaped geometry just as wash buffer droplet is positioned via electrowetting for merging with bead droplet 514.

FIG. 5B shows another step in a process of washing beads using shape-assisted merging of droplets. In this step, bead droplet 514 and washed droplet 516 are merged. Merging of bead droplet 514 and wash droplet 516 provides for redistribution of beads 518.

FIGS. 5C and 5D show another step in a process of washing beads using shape-assisted merging of droplets. In this step, a slug of fluid 520 is extended away from magnet 512 by activating the contiguous droplet operations electrodes 510 and inactivating the intermediate droplet operations electrodes 510 outside the magnetic field of magnet 512. Fluid 520 includes wash buffer from wash buffer droplet 516 and unbound reagents from bead droplet 514. As fluid 520 is extended, beads 518 remain concentrated on magnet 512.

FIG. 5E shows yet another step in a process of washing beads using shape-assisted merging of droplets. In this step, a fluid 520 is split using droplet operations to form supernatant droplet 522. Supernatant droplet 522 includes unbound reagents such as unbound reporter antibody from bead droplet 514. Supernatant droplet 522 is typically discarded in a waste well (not shown). FIGS. 5A through 5E show the set of droplet operations that comprise a wash cycle. Several wash cycles may be performed to provide for sufficient removal of unbound material.

In an alternative embodiment, a washing protocol may use a wash droplet and a bead droplet that are circular in shape. A circular shape of a droplet may, for example, be obtained by performing droplet operations on a 2× wash droplet and a 2× bead droplet using only one droplet operations electrode each. Because a 2× droplet (i.e., footprint is approximately 2 times the area of one droplet operations electrode) is much larger than a single droplet operations electrode, the droplet takes a more rounded shape.

Figure 5:
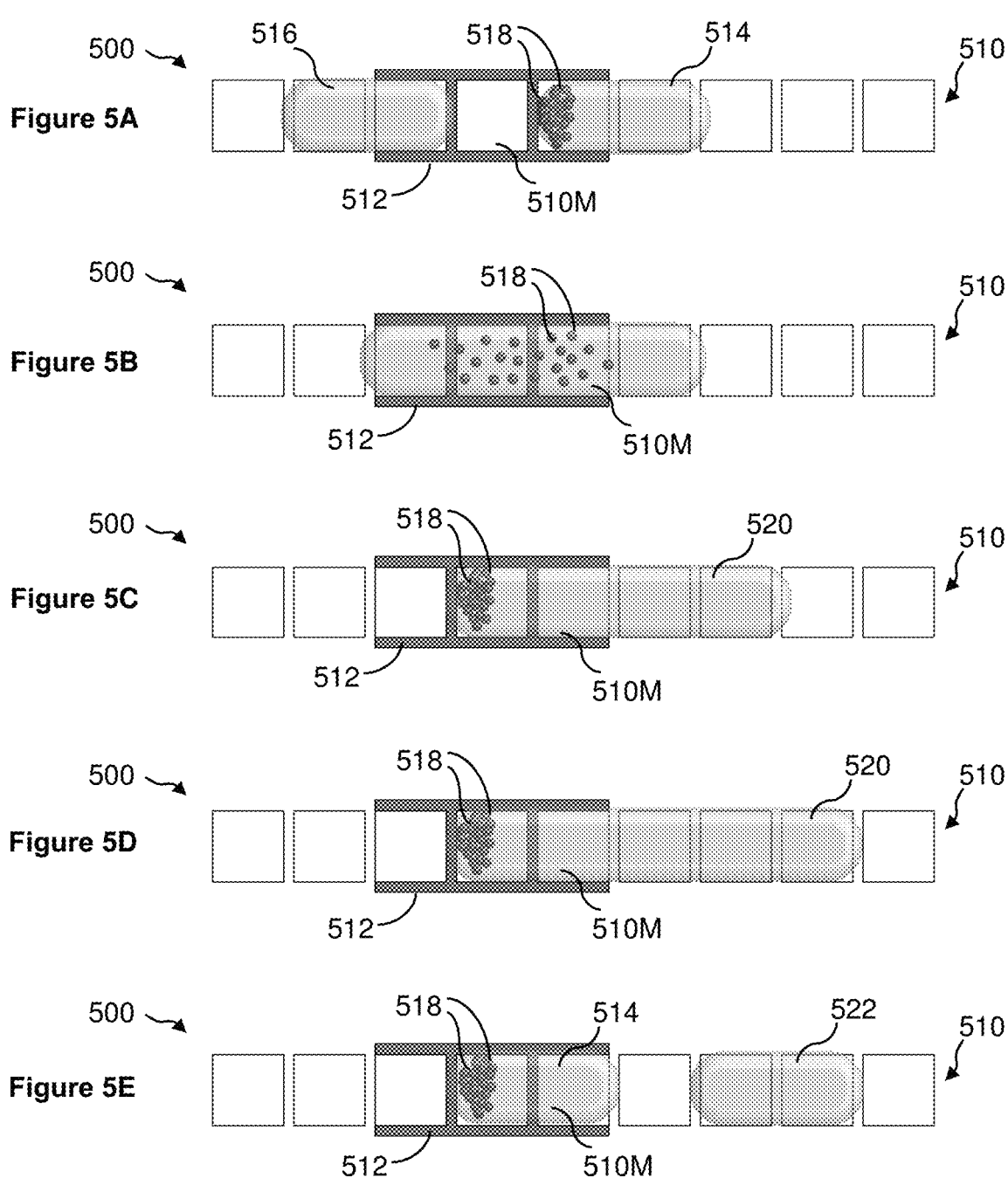
FIGS. 5A, 5B, 5C, 5D, and 5E show a top view of a region of a droplet actuator and a process of washing magnetically responsive beads using shape-assisted merging of droplets.
Figure 6:
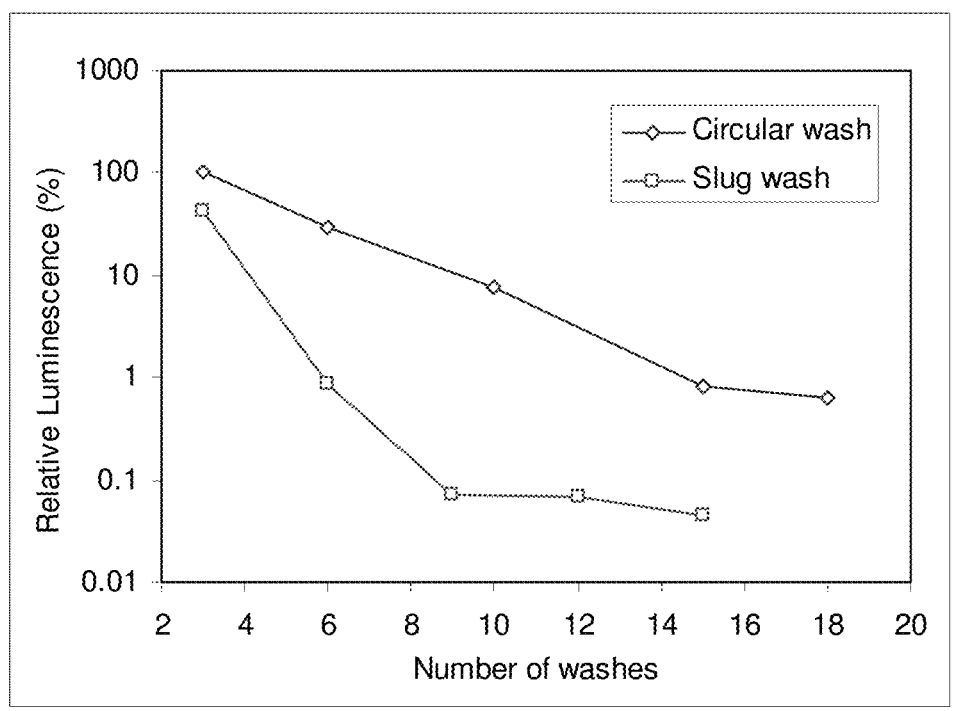
FIG. 6 shows a plot of a comparison of washing protocols between slug shaped and circular shaped wash droplets on immunoassay performance measured in chemiluminescence.

FIG. 6 shows a plot 600 of a comparison of washing protocols between slug shaped and circular shaped wash droplets on immunoassay performance measured in chemiluminescence. In both protocols, incubation was performed using the off-magnet incubation protocol of FIG. 2 for 3 minutes. Each wash cycle takes about 10 seconds in a slug-based protocol of FIG. 5 and about 14 seconds in a circular droplet protocol.

As shown is FIG. 6, a washing protocol performed using slugs of fluid (or elongated droplets as shown in FIG. 5), wherein a 2× wash buffer droplet and a 2× bead droplet were operated using two electrodes, a sufficient wash level was achieved using fewer wash cycles when compared to washing using circular shaped droplets. In a slug-based washing protocol, mixing was minimized and the bulk of the unbound material from the supernatant was replaced with fresh wash buffer at each cycle. In a circular-droplet based protocol, mixing was ensured by operating the 2× droplets using only one electrode each. Also, the dispersion of magnetically responsive beads in the lateral plane (X-Y direction) was higher in the slug-based protocol when a fresh wash buffer droplet was merged with a bead droplet. Greater dispersion of magnetically responsive beads in the merged droplet enables any unbound antibody trapped in the interstices to diffuse into the supernatant and be washed away in subsequent washes. In this example, sufficient wash levels were achieved in about 10 wash cycles using a slug-based washing protocol compared to >18 wash cycles in a circular droplet based wash protocol.

The washing behavior has two distinct regimes, one regime where washing may be very pronounced and the second where the washing may be subtle. In the slug based washing case, the washing is pronounced with each wash cycle up to about 9 cycles and after that the effect of washing is almost negligible. In the circular droplet protocol, the washing effect is pronounced until about the 15th wash; although the wash efficiency is less than that observed for the slug-based protocol. Washing is only marginally effective for the circular droplet protocol between about the 15th and 18th washes with only a slight reduction in signal with each cycle. This could happen because all the free unbound material may be washed away in the first few cycles and after that washing only removes the unbound material trapped between the beads.

FIGS. 7A, 7B, 7C, and 7D illustrate top views of an example of a region of a droplet actuator 500 of FIGS. 5A through 5E and show a process of resuspending magnetically responsive beads between wash cycles. The method of the invention of FIGS. 7A through 7D is an example of a sequence in a wash method that uses a series of droplet resuspension cycles to resuspend the magnetically responsive beads between wash cycles such as a wash cycle shown in FIG. 5. The resuspension cycles provide sufficient resuspension of the beads such that unbound material from the interstices of bead aggregates may be effectively removed.

FIG. 7A shows the first step in a process of resuspending magnetically responsive beads between wash cycles. In this step, bead droplet 514 that includes magnetically responsive beads 518 is transported via electrowetting away from magnet 512 in the direction of arrow A.

FIGS. 7B, 7C, and 7D show the process steps of transporting bead droplet 514 along a path of droplet operation electrodes 510 in the direction of arrow A. Three transport operations are shown in FIGS. 7B, 7C, and 7D, but any number of transport operations may be used to comprise a resuspension cycle. Transporting of bead droplet 514 provides for sufficient resuspension of beads 518 such that unbound material from the interstices of bead aggregates may be effectively removed in subsequent wash cycles.

A complete wash protocol may include a series of wash cycles, such as the slug based wash cycles of FIG. 5, interspersed with a one or more resuspension cycles of FIG. 7. Depending on the sensitivity of the assay required and the time to result requirement, any number of wash cycles may be interspersed with any number of resuspension cycles. For example, a complete wash protocol sequence may include, for example, four wash cycles, four resuspension cycles, and four wash cycles. A complete wash protocol sequence ends at a wash cycle.

Figure 8A:
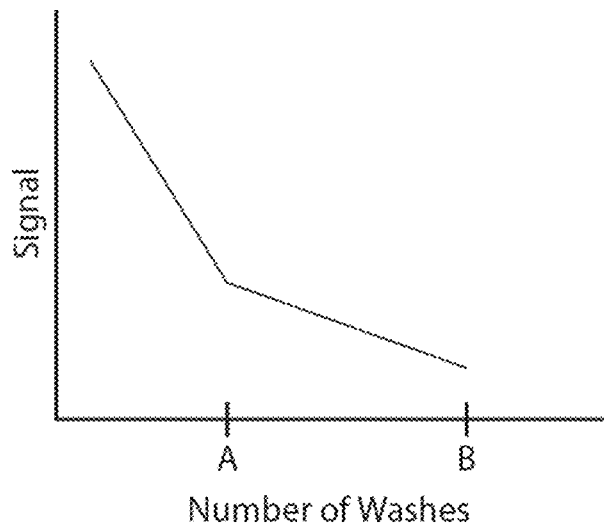
FIGS. 8A and 8B show plots of a comparison of washing protocols of FIG. 5 without resuspension cycles and with resuspension cycles, respectively.
Figure 8B:
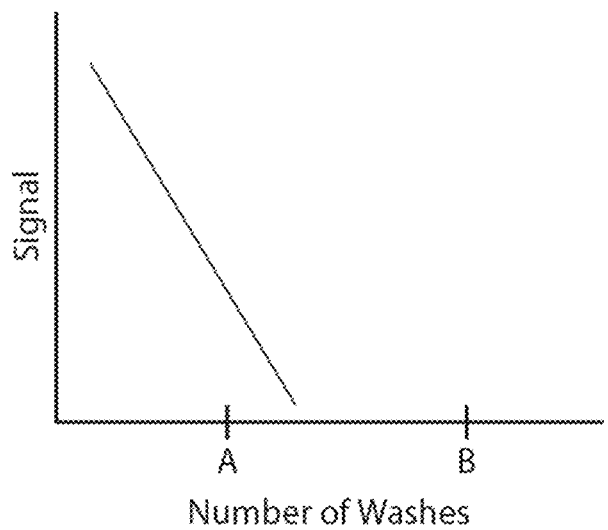

FIGS. 8A and 8B show plots of a comparison of washing protocols of FIG. 5 without resuspension cycles and with resuspension cycles, respectively. As shown in FIG. 8A, a washing protocol in the absence of one or more resuspension cycles provides an initial drop in signal after a number of wash cycles (A). As the number of wash cycles increase (B), there is a further reduction in signal that may be due to loss of unbound material from the interstices of bead aggregates.

As shown in FIG. 8B, a washing protocol that includes one or more resuspension cycles provides more efficient removal of unbound material to a near zero level using fewer numbers of wash cycles (A).

Figure 9:
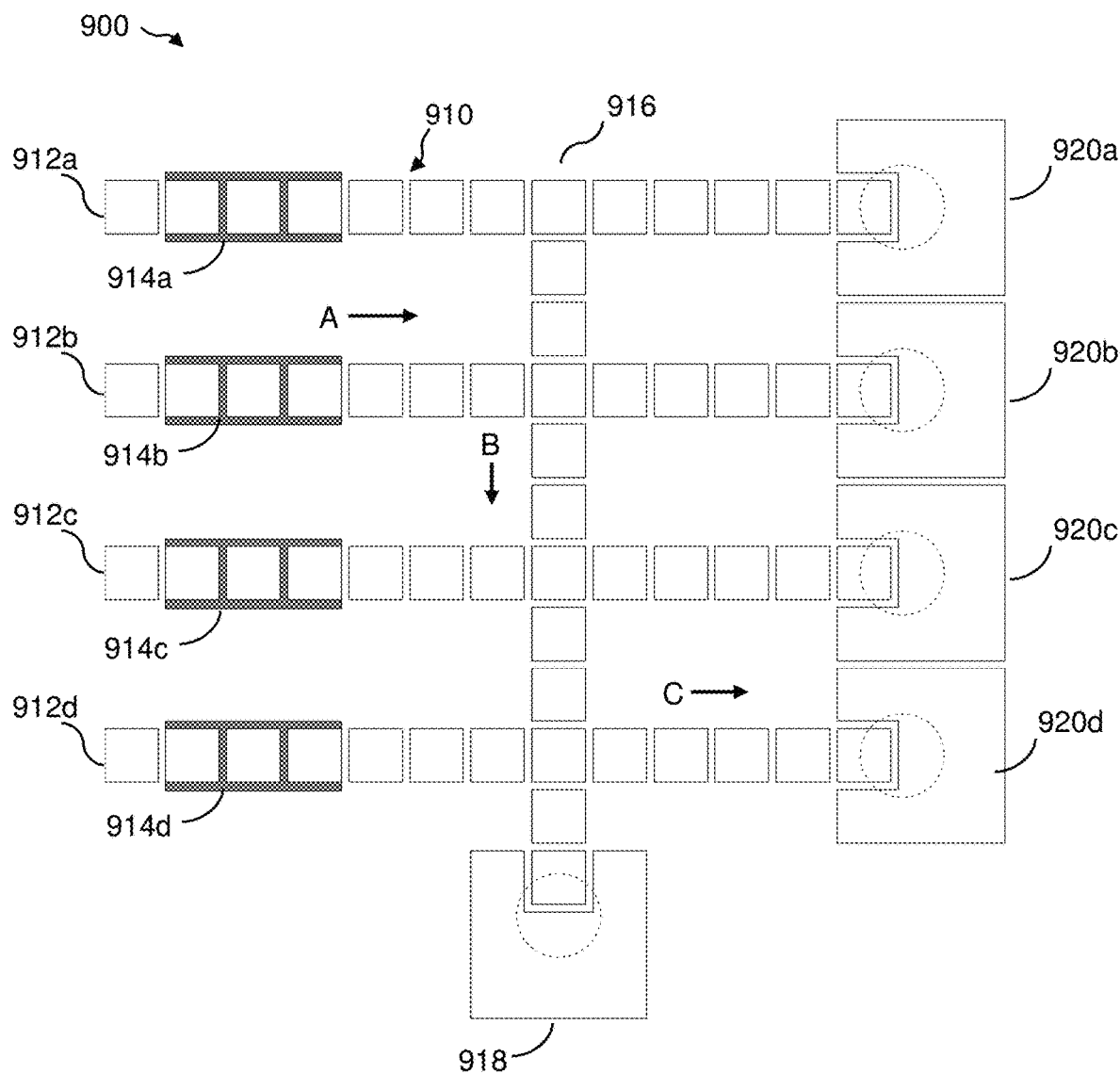
FIG. 9 illustrates a top view of a region of a droplet actuator 900 that includes multiple waste wells.

FIG. 9 illustrates a top view of a region of a droplet actuator 900 that includes multiple waste wells. In this embodiment, multiple waste wells are provided to improve the efficiency (e.g., time to result) of a bead washing protocol such as a bead washing protocol shown in FIG. 5.

As illustrated, droplet actuator 900 includes an array of droplet operations electrodes 910 (e.g., electrowetting electrodes) configured to provide wash lanes 912a, 912b, 912c, and 912d, and a single waste lane 916. Wash lanes 912a, 912b, 912c, and 912d may include magnets 914a, 914b, 914c, and 914d, respectively, and waste wells 920a, 920b, 920c, and 920d, respectively. Waste lane 916 may include a waste well 918.

In operation, droplet actuator 900 may be used to conduct a bead washing protocol on four different samples in wash lanes 912a through 912d. In a bead washing protocol, the supernatant droplet(s) that contain unbound material, such as unbound antigen and secondary reporter antibody, is typically discarded in a waste well. In one example, a bead washing protocol may use a single waste well 918. In this example, a single waste lane 916 that includes waste well 918 may be used to transport supernatant (i.e., waste) droplets from wash lanes 912a through 912d.

In this example, supernatant (i.e., waste) droplets from wash lanes 912a through 912d may be transported via electrowetting in the direction of Arrow A to wash lane 916. Individual supernatant droplets may then be transported in waste lane 916 in the direction of Arrow B to waste well 918. Because waste lane 916 is common to wash lanes 912a through 912d, supernatant droplets must be transported serially (i.e., one after another).

In an alternative example, individual waste wells 920a through 920d may be provided for each wash lane 912a through 912d, respectively. In this example, supernatant droplets may be transported simultaneously in the direction of arrow C to individual waste wells 920a through 920d. Multiple, individual waste wells provide for increased efficiency (e.g., time to result) in a washing protocol. Multiple waste wells also provide for a reduction in the number of droplet operations electrodes 910 that are required to shuttle a supernatant droplet to a waste well. A reduction in the number of operations electrodes 910 that may be used to transport a supernatant droplet also provides for a reduction in the potential for cross-contamination of subsequent droplets used in a protocol.

Bead-Mediated Droplet Splitting

FIGS. 10A, 10B, and 10C show a top view of a region of a droplet actuator 1000 and a process of separating beads from a sample droplet. The method of the invention of FIGS. 10A through 10C is an example of a method wherein magnetically responsive beads are split from a circular shaped droplet.

Droplet actuator 1000 may include a path or array of droplet operations electrodes 1010 (e.g., electrowetting electrodes). A magnet 1014 is arranged in close proximity to droplet operations electrodes 1010. In particular, magnet 1014 is arranged such that certain droplet operations electrodes 1010 (e.g., 3 droplet operations electrodes 1010M) are within the magnetic field of magnet 1014. Magnet 1014 may, for example, be a permanent magnet or an electromagnet.

Droplet actuator 1000 may contain a droplet 1016 that may be transported along droplet operations electrodes 1010 via electrowetting and upon which droplet operations may be performed. Droplet 1016 may include a quantity of beads 1020, which may be magnetically responsive beads. An example of a process of separating beads from a circular droplet may include, but is not limited to, the following steps.

FIG. 10A shows a first step in a process of separating beads from a circular droplet. In this step, droplet 1016 that has beads 1020 therein is positioned at a droplet operations electrode 1010M, which is within the magnetic field of magnet 1014. Because beads 1020 are magnetically responsive, beads 1020 are attracted to magnet 1014. Because a single droplet operations electrode 1010M is active, droplet 1016 is circular in shape.

FIG. 10B shows another step in a process of separating beads from a circular droplet. In this step, droplet 1016 is transported via electrowetting away from droplet operations electrode 1010M and to the adjacent droplet operations electrode 1010. As droplet 1016 moves away from droplet operations electrode 1010M, a concentration of beads 1020 is formed at the side of droplet 1016 that is closest to magnet 1014. Because droplet 1016 is transported away from magnet 1014 one droplet operations electrode 1010 at a time, the geometry of droplet 1016 may be distorted (e.g., formation of a neck) by the concentration of beads 1020 as droplet 1016 pulls away from magnet 1020.

FIG. 10C shows yet another step in the process of separating beads from a circular droplet. In this step, droplet 1016 is transported via electrowetting further away from droplet operations electrode 1010M and to a droplet operations electrode 1010 that is yet further away. In doing so, the concentration of beads 1020 breaks away (snaps off) from droplet 1016. This occurs because one side (e.g., the side nearest magnet 1014) of droplet 1016 is subjected to a magnetic force and the opposite side (e.g., the side farthest from magnet 1014) is subjected to electrowetting force. When beads 1020 snap off of droplet 1016, a relatively small and highly concentrated bead droplet 1022 is left behind at droplet operations electrode 1010M and held immobilized by magnet 1014.

A similar result can be achieved using a barrier that permits a bead-containing droplet to be transported while restraining transport of the beads with the main body of the droplet.

FIGS. 11A, 11B, and 11C show a top view of a region of a droplet actuator 1000 of FIGS. 10A through 10C and a process of transporting beads within a droplet. The method of the invention of FIGS. 11A through 11C is an example of a method wherein magnetically responsive beads are transported within an elongated droplet away from a magnetic force.

The steps shown in FIGS. 11A, 11B, and 11C are substantially the same as those that are described in FIGS. 10A, 10B, and 10C except that, instead of processing a 1× droplet via electrowetting using one active electrode at a time, droplet 1016 is a slug-shaped 3× droplet that is processed using three active electrodes for each droplet operation.

FIGS. 11A, 11B, and 11C show the process steps of transporting beads 1020 within an elongated droplet 1016 away from magnet 1014. In this example, one side (e.g., the side nearest magnet 1014) of droplet 1016 is subjected to both a magnetic force and electrowetting force and the opposite side (e.g., the side farthest from magnet 1014) is subjected to electrowetting force. Because electrowetting force occurs on both sides of droplet 1016, all of the fluid within the droplet is electrowetted and beads 1020 are retained within droplet 1016 during droplet transport away from magnet 1014.

Figures 12A, 12B, 12C:
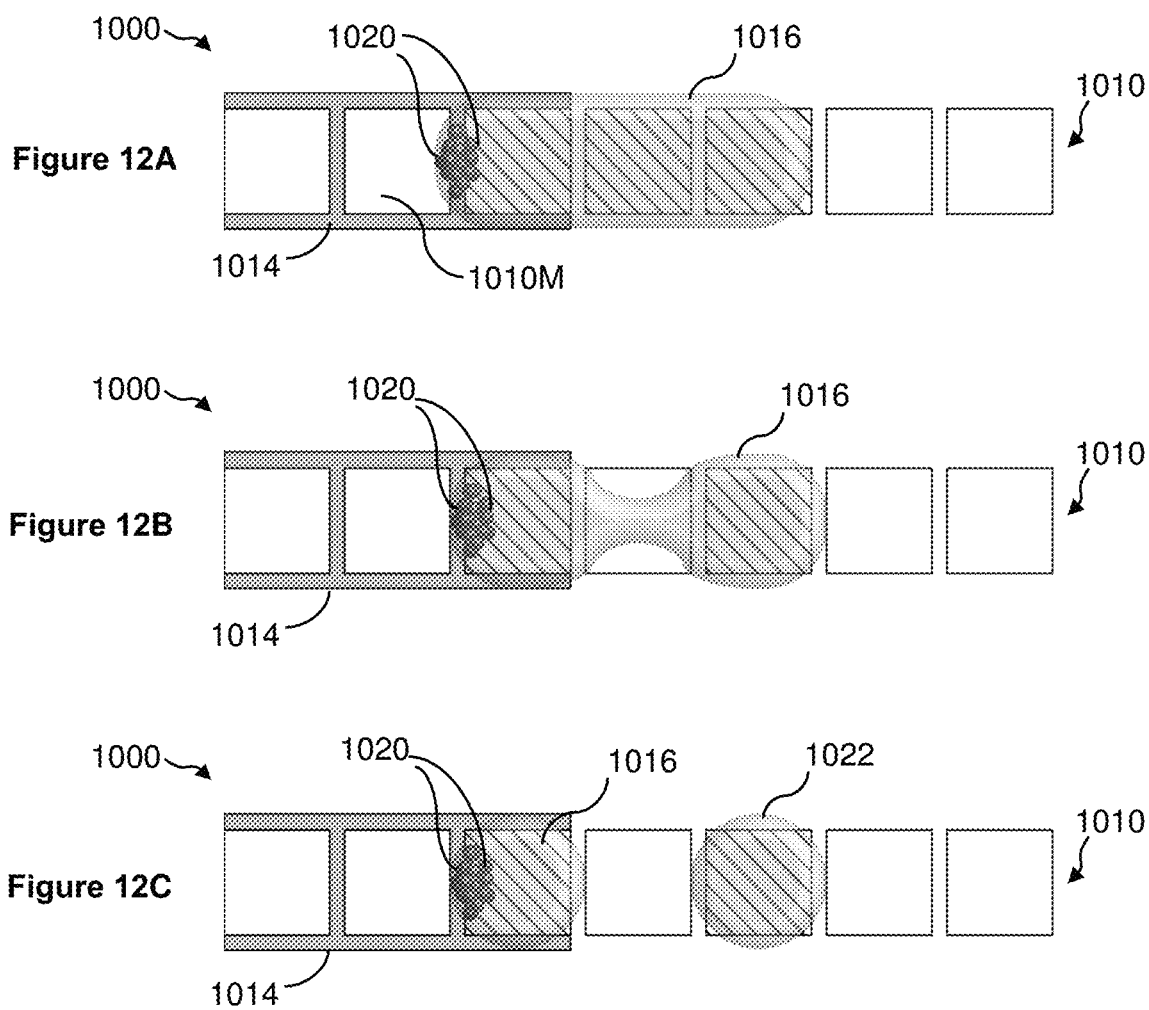
FIGS. 12A, 12B, and 12C show a top view of a region of a droplet actuator of FIGS. 10A through 10C and another process of separating beads from a sample droplet onto a magnet.

FIGS. 12A, 12B, and 12C show a top view of a region of a droplet actuator 1000 and a process of separating beads from a sample droplet onto a magnet. The method of the invention of FIGS. 12A through 12C is an example of a method wherein magnetically responsive beads are split from an elongated droplet (e.g., 3× droplet) onto a magnet. In one example, the method of the invention of FIGS. 12A through 12C may be used to dispense magnetically responsive beads onto a magnet.

The steps shown in FIGS. 12A, 12B, and 12C are substantially the same as those that are described in FIGS. 10A, 10B, and 10C except that, beads 1020 are split from an elongated 3× droplet 1016. An example of a process of dispensing beads from an elongated droplet may include, but is not limited to, the following steps.

FIG. 12A shows a first step in a process of dispensing beads from an elongated droplet. In this step, droplet 1016 that has beads 1020 therein is positioned at a droplet operations electrode 1010M, which is within the magnetic field of magnet 1014. Because beads 1020 are magnetically responsive, beads 1020 are attracted to magnet 1014. Because three droplet operations electrodes 1010 are active, droplet 1016 is elongated in shape.

FIG. 12B shows another step in a process of dispensing beads from an elongated droplet. In this step, droplet 1016 is transported away from magnet 1014 via electrowetting using one active droplet operations electrode 1010 at a time. As droplet 1016 moves away from droplet operations electrode 1010M, a concentration of beads 1020 is formed at the side of droplet 1016 that is closest to magnet 1014. Because droplet 1016 is transported away from magnet 1014 one droplet operations electrode 1010 at a time, the geometry of droplet 1016 may be distorted.

FIG. 12C shows yet another step in process of dispensing beads from an elongated droplet. In this step, droplet 1016 is transported via electrowetting further away from droplet operations electrode 1010M and to a droplet operations electrode 1010 that is yet further away. Once the sample droplet overlaps the droplet operation electrode 1010 on which droplet 1022 is to be formed, the intermediate electrode 1010 is deactivated. In doing so, droplet 1016 is split into a supernatant droplet 1022 and a smaller droplet 1016 that has beads 1020 therein.

Component Ratios

FIGS. 13A and 13B show a comparison of bench top and droplet actuator immunoassay reagent ratios and a plot of reagent concentration versus signal strength, respectively, that provide for optimum droplet based immunoassay performance.

As shown in FIG. 13A, the ratio of three components of an immunoassay, beads (i.e., capture antibody conjugated to beads), sample (e.g., serum, plasma), and secondary antibody (II° Ab) are provided. For a bench top immunoassay, a typical ratio is 1 part beads (60 μL): ½ part sample (30 μL): 1 part II° Ab (60 μL). A reagent ratio for a droplet actuator based immunoassay is typically ½ bead droplet (150 nL): 1 sample droplet (300 nL): 2 II° Ab droplets (600 nL). The use of fewer beads (i.e., ½ bead droplet or ½ concentration of beads) in a droplet actuator immunoassay provides for increased efficiency of bead washing and a sufficient reduction in non-specific binding of non-target analytes to the capture beads. In addition, the concentration of secondary antibody is the same in both bench top and droplet actuator immunoassays, but the volume of secondary antibody solution is double in the droplet actuator assay.

FIG. 13B shows the improvement in detection signal that is provided by the use of 2 droplets of secondary antibody and 2 droplets of detection substrate in a droplet actuator immunoassay.

Incubation of Magnetically Responsive Beads with Chemiluminescent Substrate

Another parameter which may influence the time to result in an immunoassay is the generation of a signal during the incubation of a chemiluminescent substrate with the washed magnetically responsive beads that contain the antigen-antibody complex.

Figure 14:
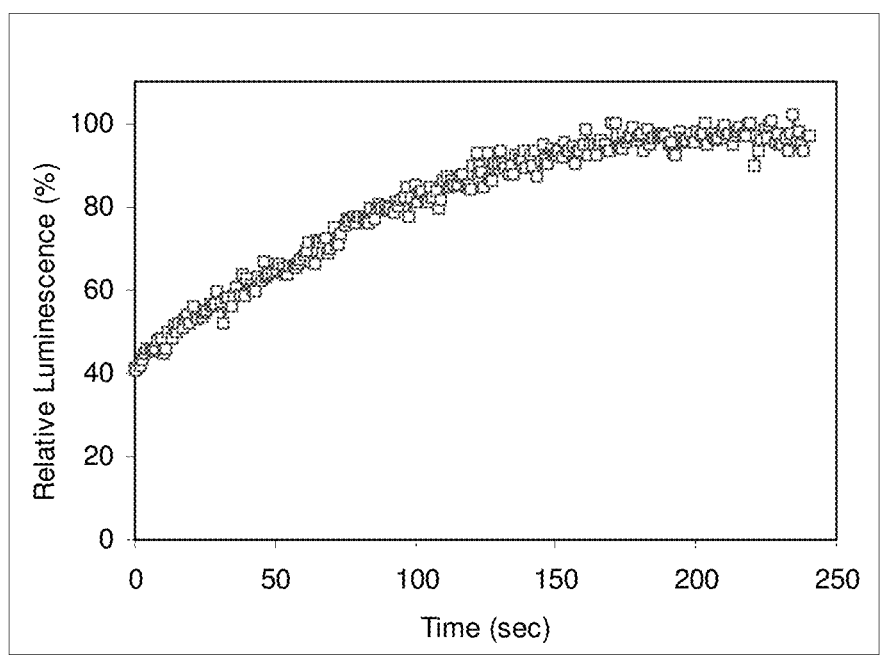
FIG. 14 shows a plot of the kinetics of a reaction between a chemiluminescent substrate and ALP reporter on magnetically responsive beads for Troponin I (TnI)

FIG. 14 shows a plot 1400 of the kinetics of a reaction between a chemiluminescent substrate and the ALP on magnetically responsive beads for Troponin I (TnI). Immunoassays were performed on TnI (100 ng/mL) using an on-magnet incubation protocol and a circular shaped droplet washing protocol. As shown in FIG. 14, about 90% of the end point signal was obtained in about 120 to about 130 seconds. For a lower concentration of the analyte, maximum signal was achieved in about <120 seconds. Based on this data, for the type of substrate used, 2 minutes may be selected as an optimum incubation time to generate maximum signal for the chemiluminescence reaction. However, if the chemiluminescence reaction is observed to behave as a flash signal instead of a glow reaction, the 2 minute incubation may be reduced to about a few seconds.

Rapid Immunoassays

Figure 3:
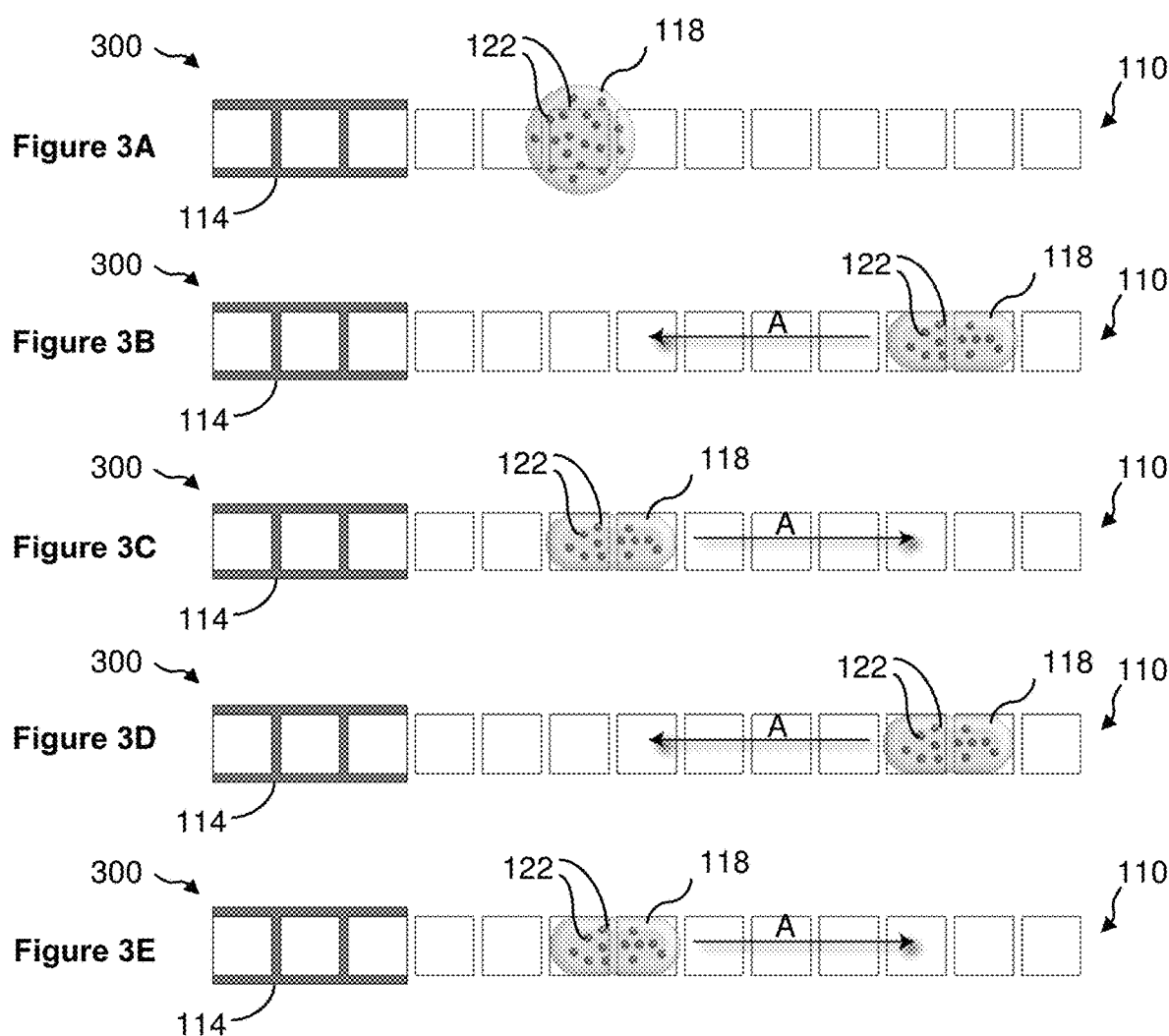
FIGS. 3A, 3B, 3C, 3D, and 3E illustrate top views of an example of a region of a droplet actuator and show a process of incubating droplets that include magnetically responsive beads completely off a magnet.

Using optimized protocols for incubation and washing, a full immunoassay was performed on TnI (5 ng/mL). Magnetically responsive beads were incubated with capture antibody, analyte and secondary antibody labeled with ALP reporter using an off-magnet incubation protocol as shown in FIG. 3. Subsequently, ten slugbased washes were performed to remove the unbound material from the supernatant (wash time approximately 2 minutes). The droplet with washed magnetically responsive beads with the antigen-antibody complex was mixed with one droplet of a chemiluminescent substrate and incubated for 2 minutes. The end point chemiluminescence was detected using a photon counter. In this example, the total time to result was approximately 10 minutes per immunoassay.

Protocol for Droplet Actuator Extraction of Human Genomic DNA

Figure 15:
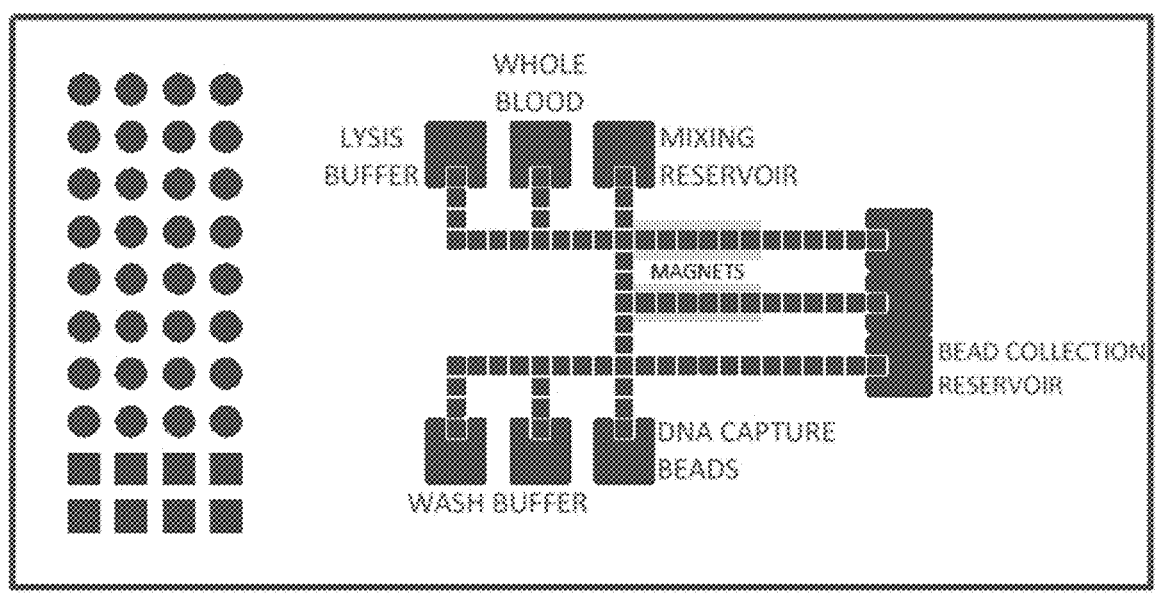
FIG. 15 is a top view of a droplet actuator that may be used for extracting DNA from a whole blood sample.

FIG. 15 is a top view of a droplet actuator 1500 that may be used for extracting DNA from a whole blood sample. The droplet actuator 1500 includes six on-actuator reservoirs, each with a capacity of 2 μL, which may be used for storing and dispensing different reagents. A typical protocol for DNA extraction on a droplet actuator may include the following steps.

In a first step, a droplet of magnetically responsive beads, such as paramagnetic Dynabeads® DNA Direct Universal from Dynal Biotech (1.05 μm diameter), suspended in a lysis buffer are dispensed from an on-chip reservoir and transported via electrowetting to a specific location on the chip. The beads, which are magnetically responsive, are held by a permanent magnet placed underneath the chip.

In another step, droplets of whole blood are dispensed from a reservoir and mixed with droplets of lysis buffer (containing 10 M NaOH) dispensed from another onchip reservoir, into a mixing reservoir in the ratio of 1:6 and mixed for about 10 seconds. Mixing was performed by dispensing a droplet and then merging the droplet back into the reservoir.

In another step, droplets of the cell lysate were then transported across the DNA capture beads in succession and the supernatant was pinched off while holding the beads.

In another step, droplets of wash buffer stored in separate on-chip reservoirs were then used to wash the beads to remove cell debris.

In another step, purified genomic DNA captured on the beads was then eluted and collected at the bead collection reservoir. The collected DNA can then be amplified either on the chip as part of an integrated sample-to-answer chip or in a commercial thermocycler for further DNA processing or diagnostic applications.

Operation Fluids

For examples of fluids that may be subjected to droplet operations using the approach of the invention, see the patents listed in section 6, especially International Patent Application No. PCT/US2006/047486, entitled, "Droplet-Based Biochemistry," filed on Dec. 11, 2006. In some embodiments, the fluid includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs, biological washes, liquids with cells, tissues, multicellular organisms, single cellular organisms, protozoa, bacteria, fungal cells, viral particles, organelles. In some embodiments, the fluid includes a reagent, such as water, deionized water, saline solutions, acidic solutions, basic solutions, detergent solutions and/or buffers. In some embodiments, the fluid includes a reagent, such as a reagent for a biochemical protocol, such as a nucleic acid amplification protocol, an affinity-based assay protocol, a sequencing protocol, and/or a protocol for analyses of biological fluids.

The fluids may include one or more magnetically responsive and/or nonmagnetically responsive beads. Examples of droplet actuator techniques for immobilizing magnetically responsive beads and/or non-magnetically responsive beads are described in the foregoing international patent applications and in Sista, et al., U.S. Patent Application No. 60/900,653, entitled "Immobilization of Magnetically-responsive Beads During Droplet Operations," filed on Feb. 9, 2007; Sista et al., U.S. Patent Application No. 60/969,736, entitled "Droplet Actuator Assay Improvements," filed on Sep. 4, 2007; and Allen et al., U.S. Patent Application No. 60/957,717, entitled "Bead Washing Using Physical Barriers," filed on Aug. 24, 2007, the entire disclosures of which is incorporated herein by reference.

Example: Cytokine Immunoassay on a Droplet Actuator

Figure 16A:
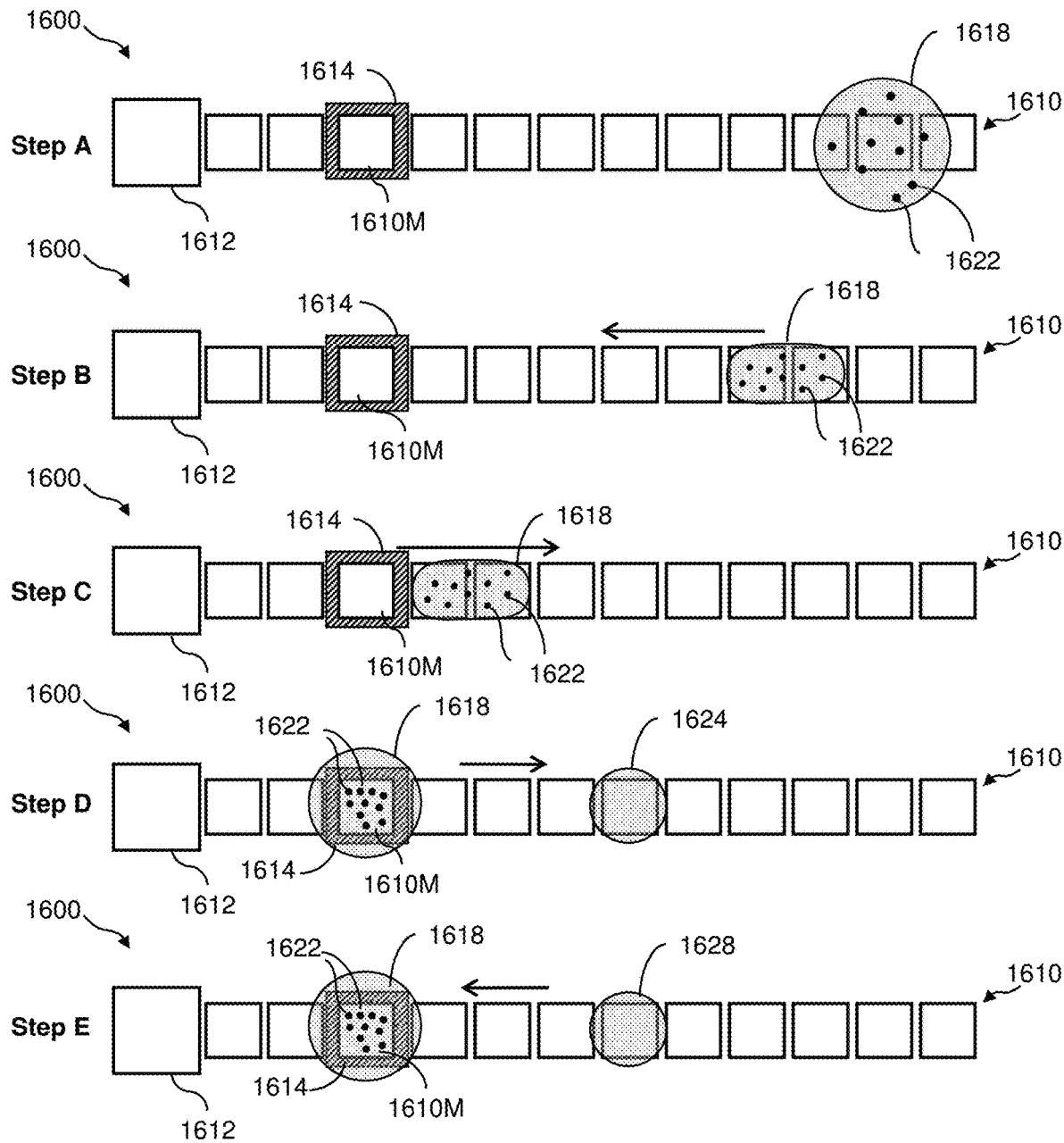
FIGS. 16A and 16B illustrate top views of an example of a portion of a droplet actuator and show a process of cytokine detection on a droplet actuator.
Figure 16B:
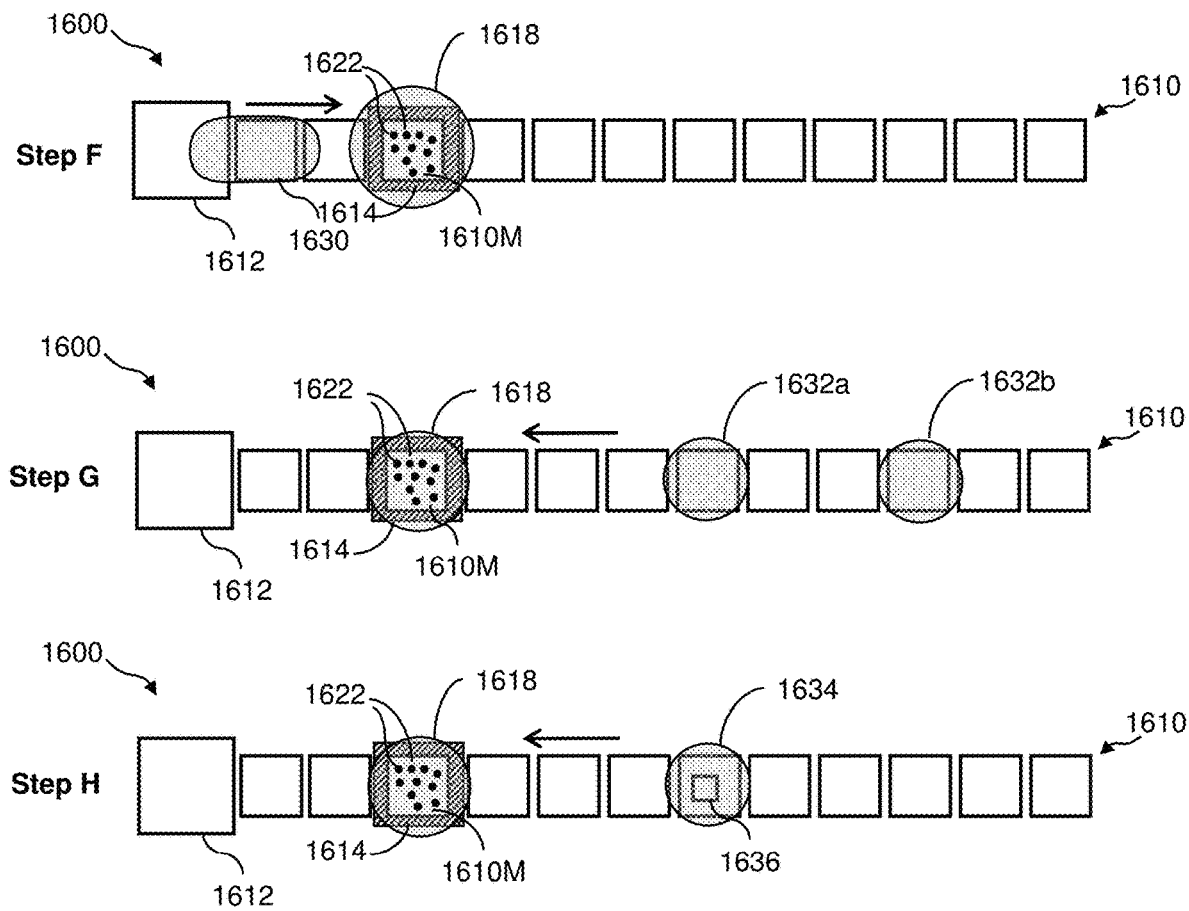

FIGS. 16A and 16B illustrate top views of an example of a portion of a droplet actuator 1600 and show a process of cytokine detection on a droplet actuator. All steps involved in the immunoassay, including sample and reagent aliquoting, incubation with antibodies, bead washing, and enzymatic detection, are fully automated and under software control.

Droplet actuator 1600 may include a path or array of droplet operations electrodes 1610 (e.g., electrowetting electrodes) and a wash reservoir 1612. A magnet 1614 is arranged in close proximity to droplet operations electrodes 1610. In particular, magnet 1614 is arranged such that a certain droplet operations electrode 1610 (e.g., droplet operations electrode 1610M) is within the magnetic field thereof. Magnet 1614 may be a permanent magnet or an electromagnet. Droplet actuator 1600 may contain a droplet 1618 that may be transported along droplet operations electrodes 1610 and upon which droplet operations may be performed.

Droplet 1618 may, for example, be a 3× droplet, meaning that its footprint is approximately 3 times the area of one droplet operations electrode 1610. Droplet 1618 may, for example, include 1 part magnetically responsive beads and 2 parts sample (e.g., an antigen to be evaluated).

Droplet 1618 may include one or more magnetically responsive beads 1622. Magnetically responsive beads 1622 are coated with a primary antibody that has an affinity for a specific target antigen. In one example, magnetically responsive beads 1622 are coated with a primary antibody that has an affinity for IL-6. In another example, magnetically responsive beads 1622 are coated with a primary antibody that has an affinity for TNF-α.

An example of a process of cytokine detection on a droplet actuator may include, but is not limited to, the following steps:

Step A of FIG. 16A shows a droplet 1618 that has magnetically responsive beads 1622 therein and is positioned at a certain droplet operations electrode 1610. In one example, droplet 1618 includes 1 part beads 1622 and 2 parts sample.

Steps B and C of FIG. 16A show an incubation process, in which droplet 1618 is repeatedly transported back and forth via droplet operations to adjacent electrodes 1610. Repeated transporting of droplet 1618 is used during incubation of beads 1622 and sample in order to provide sufficient resuspension and mixing of magnetically responsive beads 1622 for optimal antibody and antigen binding. Typically, two droplet operations electrodes 1610 may be used to transport a 3× droplet 1618, which takes on a slug shaped geometry. Elongation of droplet 1618 to a slug shape provides for sufficient flow of fluid within droplet 1618 to resuspend magnetically responsive beads 1622 therein. In one example, droplet 1618 may be incubated for 6 minutes using 2 droplet operations electrodes 1610 and transporting droplet 1618 over a span of 8 electrodes at a switching speed of 5 Hertz (Hz).

Step D of FIG. 16A shows droplet 1618 that has magnetically responsive beads 1622 therein transported to droplet operations electrode 1610M. A supernatant droplet 1624 is split off using droplet operations. Because magnetically responsive beads 1622 are attracted to magnet 1614, they are retained at magnet 1614. In one example, supernatant droplet 1624 is a 1× droplet and droplet 1618 is now a 2× droplet. Supernatant droplet 1624 that includes unbound antigen (i.e., cytokine) is discarded (not shown).

Step E of FIG. 16A shows a reagent droplet 1628 that includes secondary antibody transported via electrowetting to droplet operations electrode 1610M. Reagent droplet 1628 is merged with droplet 1618 (i.e., a 2× droplet) using droplet operations to form, for example, a 3× droplet.

In one example, reagent droplet 1628 is a 1× droplet that includes biotinylated secondary antibody that has an affinity to the target antigen. The antigen target is captured by the primary antibody which is immobilized on the beads. Merged droplet 1618 is incubated for 4 minutes using droplet operations, as described in steps B and C. Following the incubation period, droplet 1618 is transported via electrowetting to droplet operations electrode 1610M and a 1× supernatant droplet is split off using droplet operations, as described in step D, in order to yield a 2× droplet 1618. The supernatant droplet (not shown) that includes unbound secondary antibody is discarded.

After incubation with the biotinylated secondary antibody, the beads may in some embodiments be washed and then incubated with the streptavidin-peroxidase. The entire complex thus consists of beads-primary antibody-antigen-secondary antibody-streptavidin-peroxidase. Streptavidin-peroxidase may be substituted with streptavidin-alkaline phosphatase.

Step F of FIG. 16B shows a bead washing step, in which a wash droplet 1630 is transported from wash reservoir 1612 along droplet operations electrodes 1610 and across droplet 1618, which is retained at droplet operations electrode 1610M. As wash droplet 1630 passes across magnet 1614, droplet merge and split operations occur with droplet 1618 (i.e., a 2× droplet). In one example, wash droplet 1630 is a 2× droplet that has a slug geometry and the washing protocol is repeated 5 times. Following bead washing, a 1× supernatant droplet is split off from droplet 1618, as described in step D of FIG. 16A, in order to yield a 1× droplet 1618. The supernatant droplet (not shown) is discarded.

Step G of FIG. 16B shows one or more reagent droplets 1632 (e.g., 1632a, 1632b) transported to droplet operations electrode 1610M. In one example, reagent droplet 1632a that includes a blocking agent (e.g., Synblock) and reagent droplet 1632b that includes a streptavidin-enzyme conjugate (e.g., streptavidinalkaline phosphatase (ALP) or streptavidin-horseradish peroxidase) are transported to droplet operations electrode 1610M and merged using droplet operations with droplet 1618. Droplet 1618 is now a 3× droplet.

Merged droplet 1618 is incubated for 4 minutes using droplet operations, as described in steps B and C of FIG. 16A. Following the incubation period, droplet 1618 is transported to droplet operations electrode 1610M and a supernatant droplet (i.e., a 1× droplet) is split off using droplet operations, as described in step D of FIG. 16A, in order to yield a 2× droplet 1618. The supernatant droplet (not shown) that includes unbound streptavidin-enzyme conjugate is discarded.

Droplet 1618 is subsequently washed, for example 15 times, as described in step F of FIG. 16B. Following bead washing, a 1× supernatant droplet is split off droplet 1618, as described in step D of FIG. 16A, in order to yield a 1× droplet 1618. The supernatant droplet (not shown) is discarded. Droplet 1618 that includes antibody-antigen sandwich is now ready for detection.

Step H of FIG. 16B shows droplet 1634 (1× droplet) that includes a detection substrate 1636 transported to droplet operations electrode 1610M and merged using droplet operations with droplet 1618. The detection substrate 1636 is converted by the enzyme conjugate into a fluorescent signal (product formation time about 1620 seconds). The chemiluminescent signal is measured by a detector (not shown) in order to determine the quantity of antigen that is present.

In some embodiments, wash buffer droplets may be transported across the detection window following each chemiluminescent droplet to clean up the detection window and the detection loop prior to the next detection.

IL-6 Results

Figure 17:
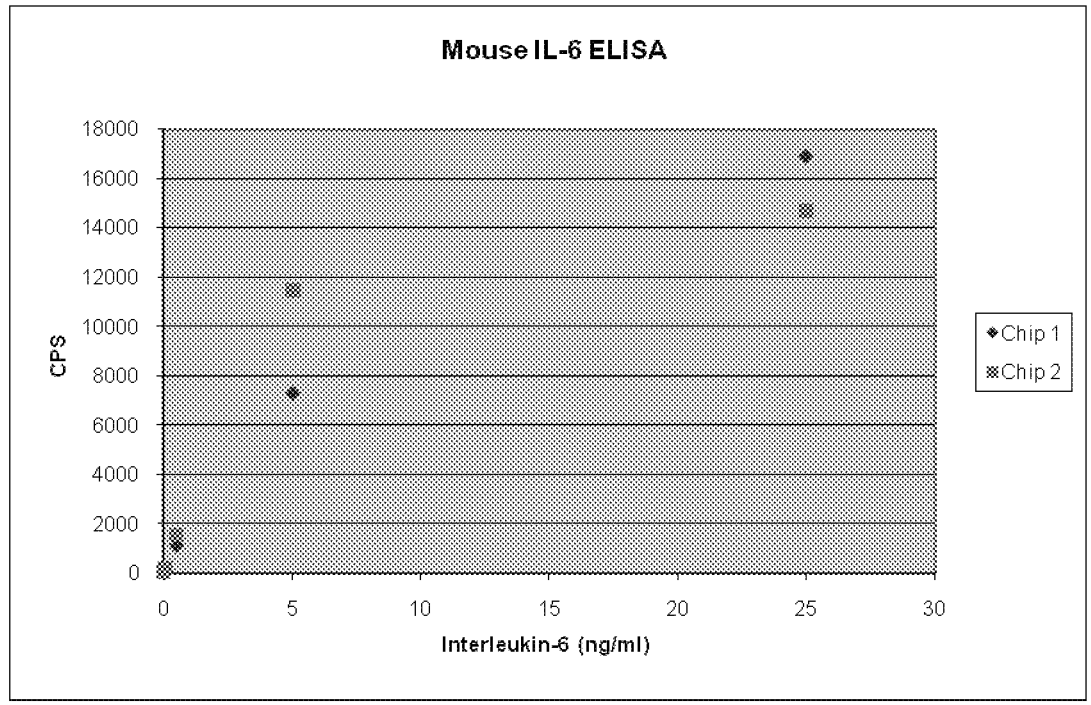
FIG. 17 shows a plot of two 5-point standard curves for cytokine IL-6.

In one embodiment, the method of the invention is used to detect IL-6. FIG. 17 shows a plot of two 5-point standard curves for cytokine IL-6. Data was generated using the cytokine detection protocol described in FIGS. 16A and 16B. In this example, two 5-point standard curves (0, 0.05, 0.5, 5, and 25 ng/mL of IL-6) were obtained in 2 runs for IL-6 performed on 2 separate droplet actuators.

TNF-α Results

Figure 18:
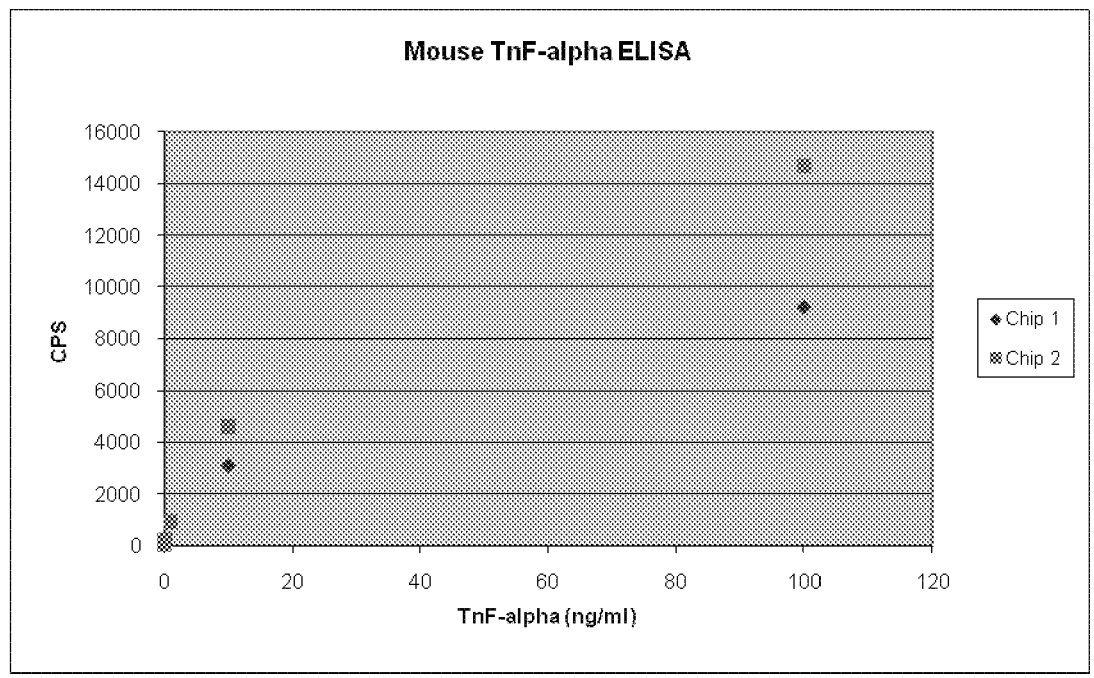
FIG. 18 shows a plot of two 6-point standard curves for cytokine TNF-α.

In an alternative embodiment, the method of the invention is used to detect TNF-α. FIG. 18 shows a plot of two 6-point standard curves for cytokine TNF-α. Data was generated using the cytokine detection protocol described in FIGS. 16A and 16B. In this example, two 6-point standard curves (0, 0.01, 0.1, 1, 10, and 100 ng/mL of TNF-α) were obtained in 2 runs for TNF-α performed on 2 separate droplet actuators.

Concluding Remarks

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

The invention claimed is:

1. A method of separating magnetically responsive beads from a droplet, the method comprising:
   (a) providing a droplet actuator comprising:
      (i) droplet operations electrodes arranged for conducting droplet operations on a droplet operations surface; and
      (ii) a magnet positioned relative to the droplet operations surface such that a droplet controlled by one or more of the droplet operations electrodes may be positioned within or away from a first region of the magnet's magnetic field capable of substantially attracting magnetically responsive beads in the droplet;
   (b) positioning a droplet having magnetically responsive beads therein within the first region of the magnetic field of the magnet to cause the magnetically responsive beads to be attracted to the magnet, and activating the droplet operations surface to cause the droplet to be circular in shape;
   (c) operating the droplet operations surface to cause the droplet to move away from the first region of the magnetic field to form a concentration of magnetically responsive beads in the droplet, and the droplet operations surface being operated to cause the droplet to be transported away from the magnet one droplet operations electrode at a time, to cause the geometry of the droplet to be distorted; and
   (d) continuing to transport the droplet away from the magnet to cause the concentration of magnetically responsive beads to break away from the droplet to result in a relatively small and highly concentrated magnetically responsive bead droplet left behind and held immobilized by the magnet.

2. The method of claim 1, wherein in (c) the concentration of magnetically responsive beads occurs at an edge of the droplet adjacent to the magnet.

3. The method of claim 1, wherein in (b) the droplet is positioned at a droplet operations electrode within the first region of the magnetic field of the magnet.

4. The method of claim 1, wherein in (c) the droplet is caused to move from the droplet operations electrode within the first region of the magnetic field partially to an adjacent droplet operations electrode away from the magnet.

5. The method of claim 1, wherein the droplet comprises a sample comprising a target substance, and the magnetically responsive beads comprise beads having an affinity for the target substance.

6. The method of claim 5, wherein the target substance is at least one of a cell, a protein, a nucleic acid, and an antigen.

7. The method of claim 5, wherein the target substance is a cytokine.

8. The method of claim 1, wherein the droplet comprises, by volume, one part magnetically responsive beads to one part sample.

9. The method of claim 1, wherein the droplet comprises, by volume, one part sample plus magnetically responsive beads to one part secondary reporter antibodies.

10. The method of claim 1, wherein the magnet is positioned such that three droplet operations electrodes are within the magnetic field of the magnet.

11. The method of claim 1, wherein the magnet is one of a permanent magnet and an electromagnet.

12. The method of claim 1, wherein the droplet transport involves electrowetting.

13. The method of claim 1, wherein the droplet transported has a footprint approximately two times the area of any one of the droplet operations electrodes.

14. The method of claim 1, wherein the droplet transported has a footprint approximately three times the area of any one of the droplet operations electrodes.

15. The method of claim 1, wherein the magnetically responsive beads are coated with a primary antibody with an affinity for a specific target antigen.

16. A method of separating magnetically responsive beads from a droplet, the method comprising:
(a) providing a droplet actuator comprising:
    (i) droplet operations electrodes arranged for conducting droplet operations on a droplet operations surface; and
    (ii) a magnet positioned relative to the droplet operations surface such that a droplet controlled by one or more of the droplet operations electrodes may be positioned within or away from a first region of the magnet's magnetic field capable of substantially attracting magnetically responsive beads in the droplet;
(b) positioning an elongated droplet containing magnetically responsive beads over at least three active droplet operations electrodes that include an intermediate droplet operation electrode, the at least three droplet operations electrodes positioned within the first region of the magnetic field of the magnet to cause the magnetically responsive beads to be attracted to the magnet;
(c) operating the droplet operations surface to cause the droplet to move away from the first region of the magnetic field to form a concentration of magnetically responsive beads in the droplet, and the droplet operations surface being operated to cause the droplet to be transported away from the magnet one droplet operations electrode at a time, to cause the geometry of the droplet to be distorted; and
(d) deactivating an intermediate droplet operations electrode to split the droplet into a supernatant droplet and a smaller droplet containing the beads held immobilized by the magnet.

17. The method of claim 16, wherein the droplet comprises a sample comprising a target substance, and the magnetically responsive beads comprise beads having an affinity for the target substance.

18. The method of claim 17, wherein the target substance is at least one of a cell, a protein, a nucleic acid, and an antigen.

19. The method of claim 17, wherein the target substance is a cytokine.

20. The method of claim 16, wherein in (c) the concentration of magnetically responsive beads occurs at an edge of the droplet adjacent to the magnet.

* * * * *

UNITED STATES PATENT AND TRADEMARK OFFICE
CERTIFICATE OF CORRECTION

PATENT NO. : 10,585,090 B2
APPLICATION NO. : 16/132175
DATED : March 10, 2020
INVENTOR(S) : Vamsee K. Pamula et al.

Page 1 of 1

It is certified that error appears in the above-identified patent and that said Letters Patent is hereby corrected as shown below:

On the Title Page

On Page 2, Column 1, item (60) Related U.S. Application Data, Line 16, delete "continuation-in-part" and insert -- continuation --, therefor.

On Page 2, Column 1, item (60) Related U.S. Application Data, Line 21, delete "continuation" and insert -- continuation-in-part --, therefor.

Signed and Sealed this
Second Day of June, 2020

Andrei Iancu
*Director of the United States Patent and Trademark Office*